US009801573B2

(12) United States Patent
Saito

(10) Patent No.: US 9,801,573 B2
(45) Date of Patent: Oct. 31, 2017

(54) ENDOSCOPE SYSTEM, PROCESSOR DEVICE, AND METHOD FOR OPERATING ENDOSCOPE SYSTEM

(71) Applicant: FUJIFILM Corporation, Tokyo (JP)

(72) Inventor: Takaaki Saito, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 368 days.

(21) Appl. No.: 14/172,565

(22) Filed: Feb. 4, 2014

(65) Prior Publication Data

US 2014/0155717 A1 Jun. 5, 2014

Related U.S. Application Data

(63) Continuation of application No. PCT/JP2012/072462, filed on Sep. 4, 2012.

(30) Foreign Application Priority Data

Sep. 5, 2011 (JP) .................................. 2011-193184

(51) Int. Cl.
  *A61B 5/1455* (2006.01)
  *A61B 5/145* (2006.01)
  (Continued)

(52) U.S. Cl.
  CPC ...... *A61B 5/14542* (2013.01); *A61B 1/00009* (2013.01); *A61B 1/063* (2013.01);
  (Continued)

(58) Field of Classification Search
  CPC ... A61B 5/1459; A61B 5/031; A61B 5/14542; A61B 1/00009; A61B 1/0653;
  (Continued)

(56) References Cited

U.S. PATENT DOCUMENTS 4,914,512 A * 4/1990 Sekiguchi .......... A61B 5/14551
   348/453
5,001,556 A * 3/1991 Nakamura ......... A61B 1/00009
   348/70
(Continued)

FOREIGN PATENT DOCUMENTS

| EP | 2 305 094 A1 | 4/2011 |
| JP | 4-17076 A | 1/1992 |
| JP | 2648494 B2 | 8/1997 |

OTHER PUBLICATIONS

Extended European Search Report, dated Apr. 13, 2015, for European Application No. 12830644.6.
(Continued)

*Primary Examiner* — Eric Winakur
*Assistant Examiner* — Chu Chuan (JJ) Liu
(74) *Attorney, Agent, or Firm* — Birch, Stewart, Kolasch & Birch, LLP

(57) ABSTRACT

A color image sensor captures a reflected image of narrow-band light having a wavelength range in which an extinction coefficient varies with a change in an oxygen saturation level of hemoglobin in blood. Thereby a first blue signal, a first green signal, and a first red signal are obtained. The color image sensor captures a reflected image of white light. Thereby a second blue signal, a second green signal, and a second red signal are obtained. Only an oxygen saturation level, out of two or more types of biological functional information including a blood volume and the oxygen saturation level, is obtained based on the first blue signal, the second green signal, and the second red signal. The oxygen saturation level is visualized to produce an oxygen saturation image.

13 Claims, 18 Drawing Sheets

(51) Int. Cl.
*A61B 1/00* (2006.01)
*A61B 1/06* (2006.01)
*G06T 7/00* (2017.01)
*A61B 5/00* (2006.01)
*A61B 5/1459* (2006.01)
*G06T 11/00* (2006.01)

(52) U.S. Cl.
CPC .......... *A61B 1/0638* (2013.01); *A61B 1/0646* (2013.01); *A61B 1/0653* (2013.01); *A61B 5/1459* (2013.01); *A61B 5/7425* (2013.01); *G06T 7/0012* (2013.01); *G06T 11/001* (2013.01); *A61B 1/00186* (2013.01); *G06T 2207/10024* (2013.01); *G06T 2207/10068* (2013.01); *G06T 2207/30101* (2013.01)

(58) Field of Classification Search
CPC ... A61B 1/0638; A61B 1/063; A61B 1/00186; A61B 5/1455; A61B 5/14551; A61B 1/14542; A61B 1/1459; G01N 21/8507
See application file for complete search history.

(56) References Cited

U.S. PATENT DOCUMENTS

| | | | | |
|---|---|---|---|---|
| 5,512,940 | A * | 4/1996 | Takasugi | G06T 7/0012 348/30 |
| 6,899,675 | B2 * | 5/2005 | Cline | A61B 1/00009 600/109 |
| 2004/0122291 | A1 * | 6/2004 | Takahashi | A61B 1/0638 600/180 |
| 2006/0116553 | A1 * | 6/2006 | Dunki-Jacobs | A61B 1/0653 600/179 |
| 2010/0016690 | A1 * | 1/2010 | Watson | A61B 5/14551 600/323 |
| 2011/0181709 | A1 * | 7/2011 | Wright | A61B 1/00009 348/65 |

OTHER PUBLICATIONS

International Preliminary Report on Patentability and Translation of the Written Opinion of the International Searching Authority (Forms PCT/IB/338, PCT/IB/326, PCT/IB/373 and PCT/ISA/237), dated Mar. 20, 2014, for International Application No. PCT/JP2012/072462.

International Search Report issued in PCT/JP2012/072462 dated Oct. 9, 2012.

Written Opinion of the International Searching Authority issued in PCT/JP2012/072462 dated Oct. 9, 2012.

Japanese Office Action, dated Aug. 26, 2015, for Japanese Application No. 2013-532600, together with an English translation thereof.

* cited by examiner

ENDOSCOPE SYSTEM, PROCESSOR DEVICE, AND METHOD FOR OPERATING ENDOSCOPE SYSTEM

CROSS REFERENCE TO RELATED APPLICATIONS:

This application is a Continuation of PCT International Application No. PCT/JP2012/072462 filed on Sep. 4, 2012, which claims priority under 35 U.S.C §119(a) to Patent Application No. 2011-193184 filed in Japan on Sep. 5, 2011, all of which are hereby expressly incorporated by reference into the present application.

BACKGROUND OF THE INVENTION

1. Field of the Invention

The present invention relates to an endoscope system, a processor device, and a method for operating an endoscope system, for visualizing information related to an oxygen saturation level of hemoglobin in blood as an oxygen saturation image.

2. Description Related to the Prior Art

Recently, endoscope systems comprising a light source device, an endoscope device, and a processor device have been widely used in medical care. In addition to normal light observation using broadband white light as illumination light, blood-vessel-enhanced observation has come into practice. In the blood-vessel-enhanced observation, narrow-band light with narrowband wavelengths is used to enhance blood vessels in an observation area in a display.

Furthermore, absorption properties of a blood vessel and light scattering properties of living tissue are used to extract biological functional information related to a blood vessel from an image signal obtained from the endoscope device. The biological functional information related to a blood vessel includes an oxygen saturation level of hemoglobin in blood and a depth of the blood vessel. The extracted biological functional information is visualized. For example, in Japanese Patent No. 2648494, different colors are assigned according to the oxygen saturation levels. A pseudo color oxygen saturation image is produced based on the assigned colors. The use of such oxygen saturation image facilitates finding a cancer which causes the oxygen saturation level exceptionally low, for example. Thereby diagnostic performance improves.

Generally, reflectivity of light in living tissue varies depending on three factors: an oxygen saturation level of hemoglobin in blood, a depth of a blood vessel, and a blood volume (which corresponds to the size of the blood vessel or density of the blood vessels). Although the Japanese Patent No. 2648494 is capable of visualizing distribution of the oxygen saturation levels as an image and displaying the image, influences of the depth of the blood vessel and a change in the blood volume on the oxygen saturation level are not considered. Hence, a less reliable image in which the oxygen saturation level of hemoglobin in blood is inaccurately visualized may be displayed in the case of the Japanese Patent No. 2648494.

SUMMARY OF THE INVENTION

An object of the present invention is to provide an endoscope system, a processor device, and a method for operating an endoscope system capable of displaying a highly reliable image in which an oxygen saturation level of hemoglobin in blood is accurately visualized.

To achieve the above and other objects, the endoscope system of the present invention comprises an illuminating section, an image signal obtaining section, an image generator, and a display section. The illuminating section illuminates a subject. The image signal obtaining section receives and images reflection light from a subject illuminated by the illuminating section, to obtain a first image signal, a second image signal, and a third image signal. The first image signal corresponds to first reflection light including a first wavelength range in a blue region. An extinction coefficient varies in accordance with an oxygen saturation level of hemoglobin in blood in the first wavelength range. The second image signal corresponds to second reflection light including a second wavelength range in a red region. The third image signal is used for standardizing the first and the second image signals. The third image signal corresponds to third reflection light including a third wavelength range in a green region. The third wavelength range differs from the first and the second wavelength ranges. The image generator produces an oxygen saturation image based on the first to the third image signals. The oxygen saturation level is visualized in the oxygen saturation image. The display section displays the oxygen saturation image.

It is preferable that the endoscope system further comprises a standardization signal obtaining section for obtaining a first standardization signal and a second standardization signal. The first standardization signal is obtained by standardizing the first image signal with the third image signal. The second standardization signal is obtained by standardizing the second image signal with the third image signal. The image generator uses a correlation between a first color information and a combination of the first and second standardization signals to produce the oxygen saturation image.

It is preferable that the image generator further comprises an oxygen saturation calculator and an oxygen saturation image generator. The oxygen saturation calculator obtains the oxygen saturation level not dependent on the blood volume, based on the first to the third image signals. The oxygen saturation image generator produces the oxygen saturation image based on the oxygen saturation level obtained by the oxygen saturation calculator.

It is preferable that the image signal obtaining section images the subject, illuminated with blue narrowband light, with a color image sensor, to obtain the first image signal, and the image signal obtaining section images the subject, illuminated with white light, with the color image sensor to obtain the second and the third image signals. It is preferable that the white light is pseudo white light generated by applying excitation light of a predetermined wavelength to a wavelength converter.

It is preferable that the illuminating section sequentially applies first illumination light, second illumination light, and third illumination light to the subject. The first illumination light has the first wavelength range. The second illumination light has the second wavelength range. The third illumination light has the third wavelength range. The image signal obtaining section receives and images reflection light of the sequentially applied first to third illumination light, with a monochrome image sensor, to sequentially obtain the first to the third image signals.

It is preferable that the illuminating section simultaneously applies first illumination light and fourth illumination light to the subject. The first illumination light has the first wavelength range. The fourth illumination light has the second and the third wavelength ranges. The image signal obtaining section receives and images reflection light of the simultaneously applied first and the fourth illumination light, with a color image sensor, to obtain the first to the third image signals.

It is preferable that the first wavelength range or the second wavelength range is within a range from 460 to 700 nm. It is preferable that the first wavelength range is from 460 to 480 nm, and the second wavelength range is from 590 to 700 nm, and the third wavelength range is from 540 to 580 nm.

An endoscope system of the present invention comprises an illuminating section, an image signal obtaining section, an image generator, and a display section. The illuminating section illuminates a subject. The image signal obtaining section receives and images reflection light from a subject illuminated by the illuminating section, to obtain a first image signal, a second image signal, and a third image signal. The first image signal corresponds to first reflection light including a first wavelength range in a green region. An extinction coefficient varies in accordance with an oxygen saturation level of hemoglobin in blood in the first wavelength range. The second image signal corresponds to second reflection light including a second wavelength range in a red region. The third image signal is used for standardizing the first and the second image signals. The third image signal corresponds to third reflection light including a third wavelength range in a green region. The third wavelength range differs from the first and the second wavelength ranges. The image generator produces an oxygen saturation image based on the first to the third image signals. The oxygen saturation level is visualized in the oxygen saturation image. The display section displays the oxygen saturation image.

It is preferable that the first wavelength range is from 530 to 550 nm, and the second wavelength range is from 590 to 700 nm, and the third wavelength range is from 555 to 565 nm.

An endoscope system of the present invention comprises an illuminating section, an image signal obtaining section, a standardization signal obtaining section, an image generator, and a display section. The illuminating section illuminates a subject. The image signal obtaining section receives and images reflection light from a subject illuminated by the illuminating section, to obtain a first image signal, a second image signal, and a third image signal. The first image signal corresponds to first reflection light including a first wavelength range in a blue region. An extinction coefficient varies in accordance with an oxygen saturation level of hemoglobin in blood in the first wavelength range. The second image signal corresponds to second reflection light including a second wavelength range in a red region. The third image signal is used for standardizing the first and the second image signals. The third image signal corresponds to third reflection light including a third wavelength range in a green region. The third wavelength range differs from the first and the second wavelength ranges. The standardization signal obtaining section obtains a first standardization signal and a second standardization signal. The first standardization signal is obtained by standardizing the first image signal with the third image signal. The second standardization signal is obtained by standardizing the second image signal with the third image signal. The image generator produces an oxygen saturation image with the use of a first correlation between the first standardization signal and first color information. The image generator produces a blood volume image with the use of a second correlation between the second standardization signal and second color information. The oxygen saturation level is visualized in the oxygen saturation image. The blood volume is visualized in the blood volume image. The display section displays the oxygen saturation image and the blood volume image.

An endoscope system of the present invention comprises an illuminating section, an image signal obtaining section, a standardization signal obtaining section, an image generator, and a display section. The illuminating section illuminates a subject. The image signal obtaining section receives and images reflection light from a subject illuminated by the illuminating section, to obtain a first image signal and a third image signal. The first image signal corresponds to first reflection light including a first wavelength range in a blue region. An extinction coefficient varies in accordance with an oxygen saturation level of hemoglobin in blood in the first wavelength range. The third image signal corresponds to third reflection light including a third wavelength range in a green region. The third image signal is used for standardizing the first image signal. The third wavelength range differs from the first wavelength range. The standardization signal obtaining section standardizes the first image signal with the third image signal to obtain a first standardization signal. The image generator produces an oxygen saturation image with the use of a first correlation between the first standardization signal and first color information. The oxygen saturation level is visualized in the oxygen saturation image. The display section displays the oxygen saturation image.

A processor device of the present invention comprises a receiver and an image generator. The receiver receives the first to the third image signals from the endoscope device. The image generator produces an oxygen saturation image based on the first to the third image signals. The oxygen saturation level is visualized in the oxygen saturation image. The processor is used with an endoscope device for receiving and imaging reflection light from a subject illuminated with an illuminating section, to obtain first to third image signals. The first image signal corresponds to first reflection light including a first wavelength range in a blue region. An extinction coefficient varies in accordance with an oxygen saturation level of hemoglobin in blood in the first wavelength range. The second image signal corresponds to second reflection light including a second wavelength range in a red region. The third image signal is used for standardizing the first and the second image signals. The third image signal corresponds to third reflection light including a third wavelength range in a green region. The third wavelength range differs from the first and the second wavelength ranges.

A method for operating an endoscope system comprises an illuminating step, an image signal obtaining step, an image producing step, and a displaying step. In the illuminating step, illumination light is applied from an illuminating section. In the image signal obtaining step, first to third image signals are obtained. The first to the third image signals are obtained by receiving and imaging reflection light from a subject with an image signal obtaining section. The first image signal corresponds to first reflection light including a first wavelength range in a blue region. An extinction coefficient varies in accordance with an oxygen saturation level of hemoglobin in blood in the first wavelength range. The second image signal corresponds to second reflection light including a second wavelength range in a red region. The third image signal is used for standardizing the first and the second image signals. The third image signal corresponds to third reflection light including a third wavelength range in a green region. The third wavelength range differs from the first and the second wavelength ranges. In the image producing step, an oxygen saturation image is produced based on the first to the third image signals with the use of an oxygen saturation image generator. The oxygen saturation level is visualized in the oxygen saturation image. In the displaying step, the oxygen saturation image is displayed on a display section.

According to an aspect of the present invention, an oxygen saturation image in which the oxygen saturation level is visualized is produced based on the first, the second, and the third image signals. The first image signal corresponds to the first reflection light including the first wavelength range in which the extinction coefficient varies in accordance with the oxygen saturation level of hemoglobin in blood. The second image signal corresponds to the second reflection light including the second wavelength range in which the extinction coefficient varies in accordance with the blood volume, unlike the first wavelength range. The blood volume indicates an amount of hemoglobin in blood. The third image signal is used for standardizing the first and the second image signals and corresponds to the third reflection light including the third wavelength range which differs from the first and the second wavelength ranges. A screen is displayed based on the produced oxygen saturation image. Thereby a highly reliable image in which an oxygen saturation level of hemoglobin in blood is accurately visualized is displayed.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
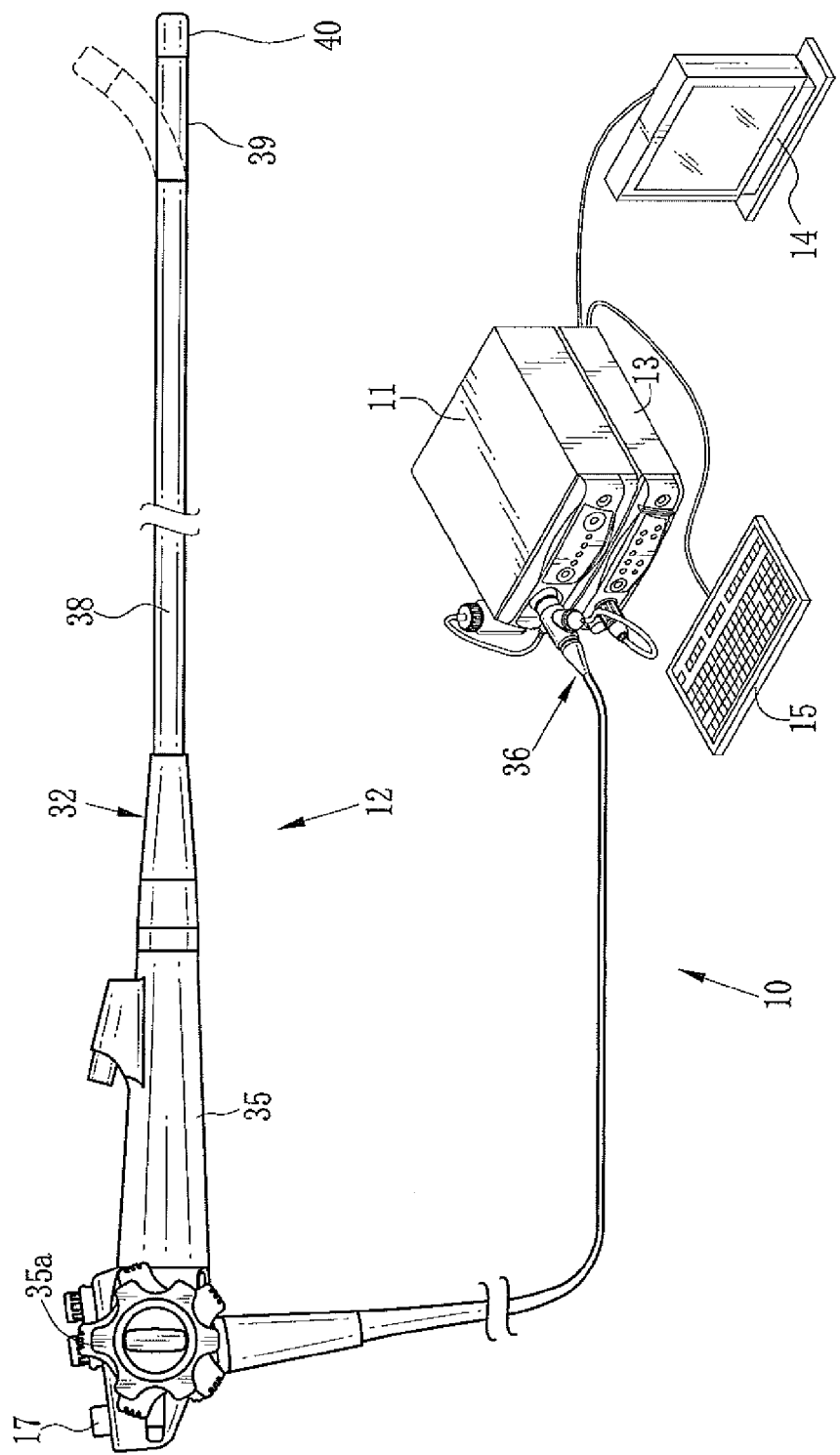
FIG. 1 is an external view of an endoscope system of a first embodiment.

As shown in FIG. 1, an endoscope system 10 of a first embodiment comprises a light source device 11, an endoscope device 12, a processor device 13, a display device 14, and an input device 15. The light source device 11 generates light for illuminating an observation area of a subject (hereinafter may referred to as the observation object). The endoscope device 12 guides the light from the light source device 11 and applies the light as illumination light to the observation object and images the observation object. The processor device 13 performs image processing on an endoscope image captured with the endoscope device 12. The display device 14 displays an endoscopic image and the like produced by the image processing. The input device 15 is composed of a keyboard or the like.

The endoscope system 10 is provided with a normal light observation mode and a biological functional information observation mode. In the normal light observation mode, a normal light image is displayed on the display device 14. The normal light image is a subject image of visible light in a wavelength range from blue to red. In the biological functional information observation mode, an oxygen saturation image and a blood volume image are displayed on the display device 14. The oxygen saturation image represents information on oxygen saturation level(s) of hemoglobin in blood in the observation object in pseudo color. The blood volume image represents information on blood volume of the observation object in pseudo color. The observation mode is switched as necessary based on a command inputted from a selection switch 17 of the endoscope device 12 or the input device 15.

A scope 32 is provided with a flexible portion 38, a bending portion 39, and a scope distal portion 40 in this order from a handle section 35 side. The flexible portion 38 is flexible, so that the flexible portion 38 bends inside the subject (body cavity) when the scope 32 is inserted. The bending portion 39 is bent by rotating an angle knob 35a disposed in the handle section 35. The bending portion 39 can be bent at any angle in vertical and horizontal directions to direct the scope distal portion 40 to a desired observation object.

Figure 2:
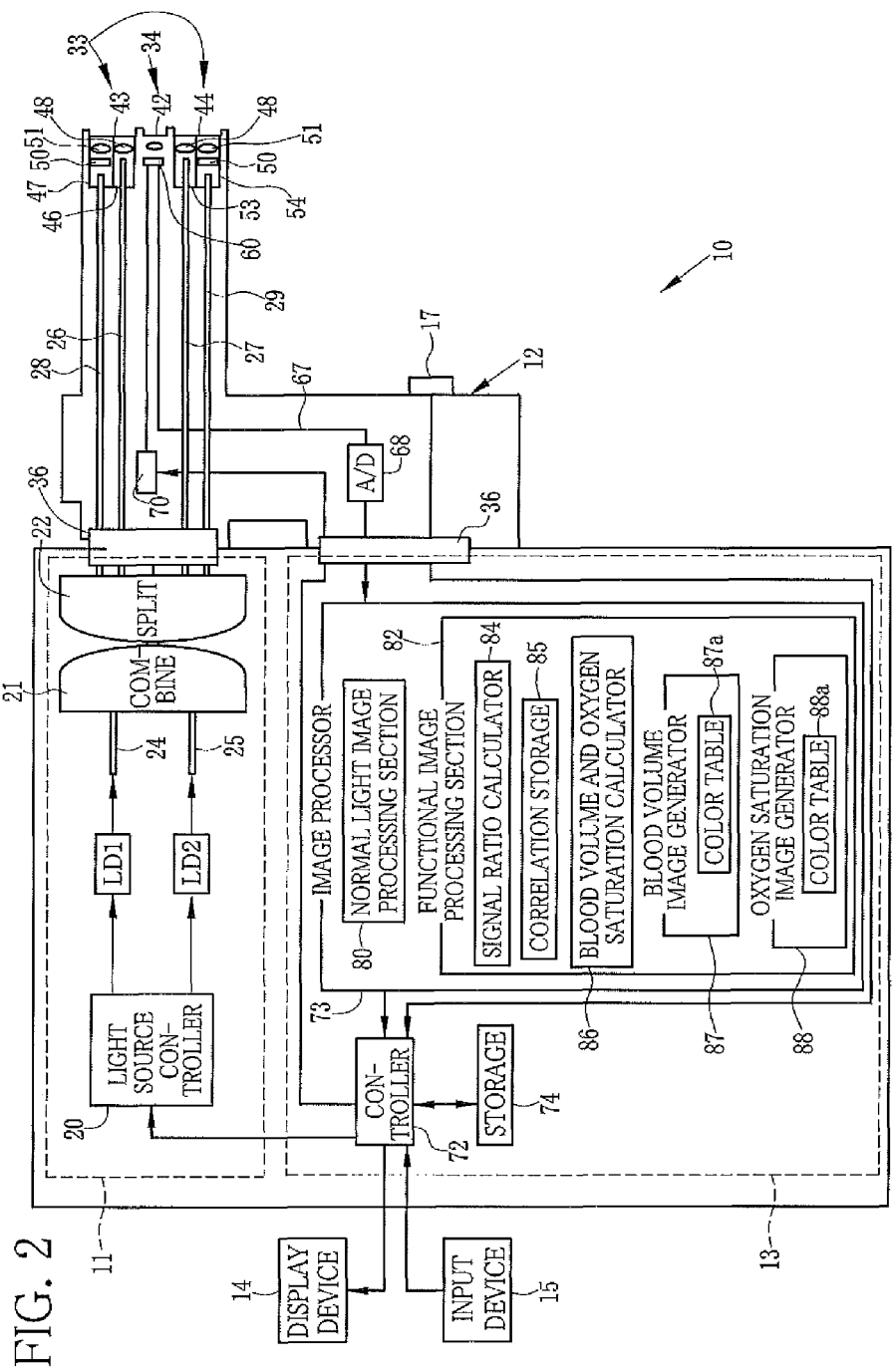
FIG. 2 is a schematic view of the endoscope system.

As shown in FIG. 2, the light source device 11 comprises two kinds of laser light sources LD1 and LD2, a light source controller 20, a combiner 21, and a splitter 22. The laser light source LD1 generates narrowband light beams (oxygen saturation measuring beams) used for measuring an oxygen saturation level. The laser light source LD2 generates excitation light beams for causing a phosphor 50 to generate white light (pseudo white light). The phosphor 50 is disposed at the distal portion of the endoscope device 12. The light beams from the laser light source LD1 are incident on an optical fiber 24 through a condenser lens (not shown). The light beams from the laser light source LD2 are incident on an optical fiber 25 through a condenser lens (not shown). Note that, for each of the laser light sources LD1 and LD2, a broad area InGaN laser diode, an InGaNAs laser diode, a GaNAs laser diode, or like can be used.

The light source controller 20 controls the laser light sources LD1 and LD2 to adjust emission timing of each of the laser light sources LD1 and LD2 and a light quantity ratio between the laser light sources LD1 and LD2 In this embodiment, in the normal light observation mode, the laser light source LD1 is turned off and the laser light source LD2 is turned on. In the biological functional information observation mode, on the other hand, the laser light sources LD1 and the LD2 are turned on alternately at predetermined time intervals.

The combiner 21 combines the light beams from the optical fiber 24 and the light beams from the optical fiber 25. The splitter 22 splits the combined light beams into four paths of light beams. Out of the four paths of light beams, the splitter 22 allows the light beams from the laser light source LD1 to be transmitted through light guides 26 and 27. The splitter 22 allows the light beams from the laser light source LD2 to be transmitted through light guides 28 and 29. Each of the light guides 26 to 29 is composed of a bundle fiber that is a plurality of optical fibers bundled together. Note that the light beams from the laser light sources LD1 and LD2 may be directly incident on the light guides 26 to 29 without using the combiner 21 and the splitter 22.

The endoscope device 12 is an electronic endoscope and comprises the scope 32 (see FIG. 1), an illuminating section 33, an imaging section 34, the handle section 35, and a connector section 36. The illuminating section 33 applies the four paths of light beams transmitted through the respective light guides 26 to 29. The single imaging section 34 images the observation object. The handle section 35 is used for bending the bending portion 39 of the scope 32 and for performing operation for observation. The connector section 36 connects the scope 32, the light source device 11, and the processor device 13 in a detachable manner.

The scope distal portion 40 is provided with the illuminating section 33 and the imaging section 34. The imaging section 34 is provided with a capture window 42 substantially at the center of the scope distal portion 40. The reflection light from the observation object is incident on the capture window 42. The illuminating section 33 comprises two illumination windows 43 and 44 provided on respective sides of the imaging section 34. Each of the illumination windows 43 and 44 projects one of the oxygen saturation measuring beams and the white light to the observation object.

Two projection units 46 and 47 are accommodated behind the illumination window 43. The projection unit 46 projects the oxygen saturation measuring beams from the light guide 26 to the observation object through a lens 48. The projection unit 47 applies the excitation light beams from the light guide 28 to the phosphor 50 to project the white light. The white light is applied to the observation object through a lens 51. Note that two projection units 53 and 54 are accommodated behind the illumination window 44. The projection unit 53 is similar to the projection unit 46. The projection unit 54 is similar to the projection unit 47.

An optical system such as an objective lens unit (not shown) is provided behind the capture window 42. The objective lens unit takes in image light from the observation object of the subject. An image sensor 60 is provided behind the objective lens unit. The image sensor 60 is a CCD (charge coupled device), a CMOS (complementary metal-oxide semiconductor), or the like. The image sensor 60 receives the image light from the observation object to image the observation object.

A light receiving surface (imaging surface) of the image sensor 60 receives the light from the objective lens unit. The image sensor 60 photoelectrically converts the received light to output an imaging signal (analog signal). An imaging controller 70 controls imaging of the image sensor 60. The imaging signal (analog signal) outputted from the image sensor 60 is inputted to an A/D converter 68 through a scope cable 67. The A/D converter 68 converts the imaging signal into an image signal (digital signal) corresponding to a voltage level of the imaging signal. After the conversion, the image signal is inputted to an image processor 73 of the processor device 13 through the connector section 36.

The processor device 13 comprises a controller 72, the image processor 73, and storage 74. The display device 14 and the input device 15 are connected to the controller 72. The controller 72 controls operations of the image processor 73, the light source controller 20 of the light source device 11, the imaging controller 70 of the endoscope device 12, and the display device 14, based on a command instructing the observation mode and the like. The command is inputted from the selection switch 17 of the endoscope device 12 or the input device 15.

Figure 3:
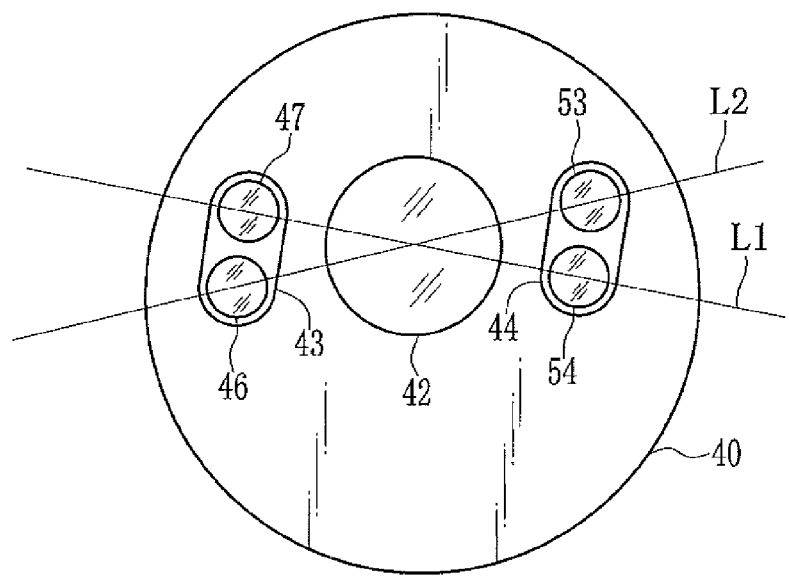
FIG. 3 is a front view of a scope distal portion.

As shown in FIG. 3, in the scope distal portion 40, the capture window 42 is disposed between the illumination windows 43 and 44. The four projection units 46, 47, 53, and 54 are arranged in a staggered configuration in which a straight line L1 between the output surfaces of the projection units 47 and 54 and a straight line L2 between the output surfaces of the projection units 46 and 53 cross each other at a center portion of the capture window 42. This arrangement prevents unevenness in the illumination. Each of the projection units 47 and 54 is provided with the phosphor 50. The projection units 46 and 53 are not provided with the phosphor 50.

The phosphor 50 includes several types of fluorescent substances, for example, YAG fluorescent substances or BAM ($BaMgAl_{10}O_{17}$). These fluorescent substances absorb a part of the excitation light beams from the laser light source LD2 to emit green to red light. When the excitation light is applied to the phosphor 50, the green to red light (fluorescence), emitted from the phosphor 50 being excited, and the excitation light, passed through the phosphor 50 without being absorbed, are combined to generate the white light (pseudo white light). Note that the phosphor may be referred to as Micro White (registered trademark) or MW.

Figure 4:
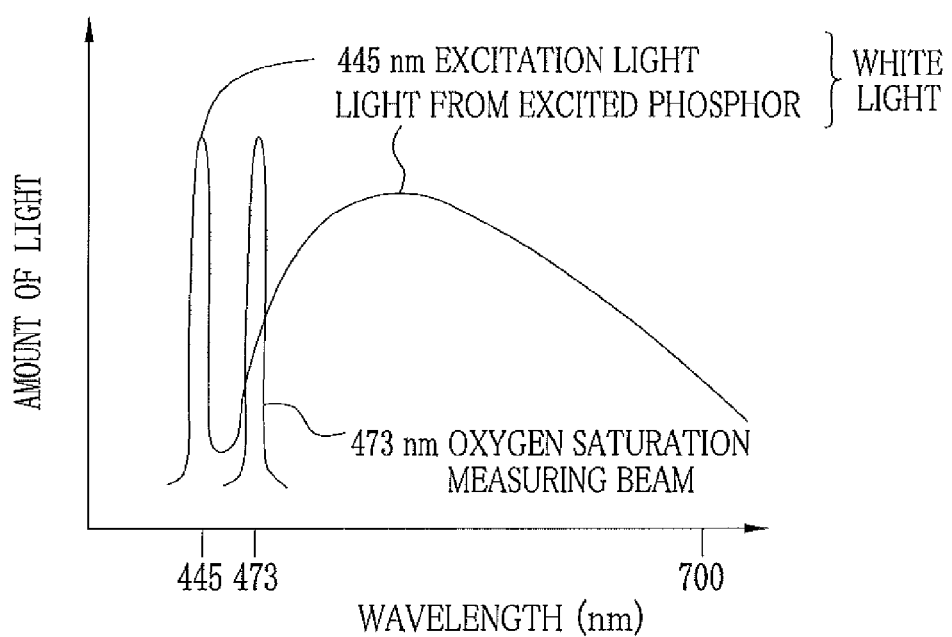
FIG. 4 is a graph illustrating emission spectra of oxygen saturation measuring beams and white light.

Hence, as shown in FIG. 4, the white light emitted from the projection units 47 and 54, each comprising the phosphor 50, has emission spectra including a wavelength range of the excitation light having the center wavelength of 445 nm and a wavelength range approximately from 450 nm to 700 nm in which emission intensity of the fluorescence generated by the excitation light increases. The oxygen saturation measuring beams emitted from each of the projection units 46 and 53, neither of which has the phosphor 50, has an emission spectrum in a wavelength range around the center wavelength of 473 nm.

Note that the white light of the present invention does not necessarily include all wavelength components of the visible light. The white light may include light in a specific wavelength range only, for example, light of a primary color, R (red), G (green), or B (blue), like the above-described pseudo white light. In other words, the white light of the present invention may contain light having the wavelength components from green to red or light having the wavelength components from blue to green, for example.

Figure 5:
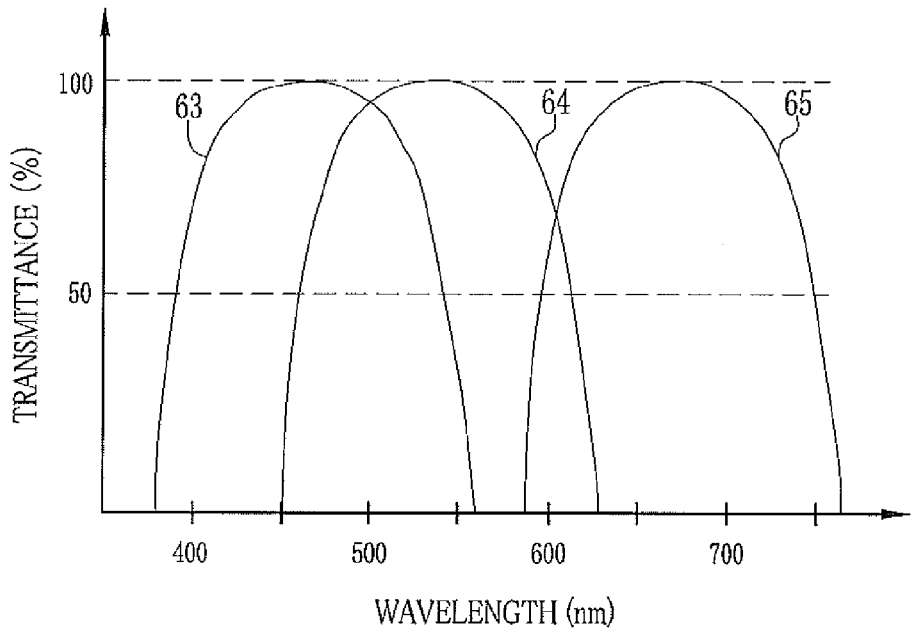
FIG. 5 is a graph illustrating spectral transmittance of R, G, and B color filters.

The image sensor 60 is a color CCD. On the light receiving surface of the image sensor 60, a plurality of R pixels each provided with an R (red) color filter, a plurality of G pixels each provided with a G (green) color filter, and a plurality of B pixels each provided with a B (blue) color filter are arranged in a matrix in groups of R, G, and B pixels. As shown in FIG. 5, the B color filter has spectral transmittance represented by a curve 63. The G color filter has spectral transmittance represented by a curve 64. The R color filter has spectral transmittance represented by a curve 65. Hence, the white light, of the reflection light reflected from the observation object, passes through all of the R, G, and B color filters. Thereby, a signal outputted from each of the R, G, and B pixels of the image sensor 60 includes information on a reflected image of the white light. On the other hand, information on a reflected image of the oxygen saturation measuring beams is mainly contained in a color signal outputted from the B or G pixel because the center wavelength of the oxygen saturation measuring beams is 473 nm.

Figure 6A:
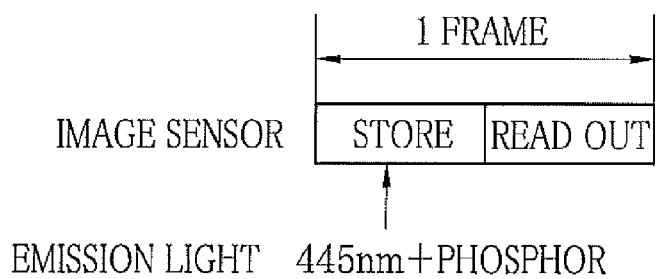
FIG. 6A is an explanatory view illustrating imaging control of an image sensor in a normal light observation mode.

The imaging controller 70 controls imaging of the image sensor 60 differently depending on an observation mode. As shown in FIG. 6A, in the normal light observation mode, two steps, a step for storing a charge obtained by photoelectric conversion of the white light (445 nm+phosphor (the white light is thus denoted in this embodiment because the white light is generated by applying the excitation light of 445 nm to the phosphor 50) and a step for reading out the stored charge, are performed in a single frame period. These two steps are repeated in the normal light observation mode.

Figure 6B:
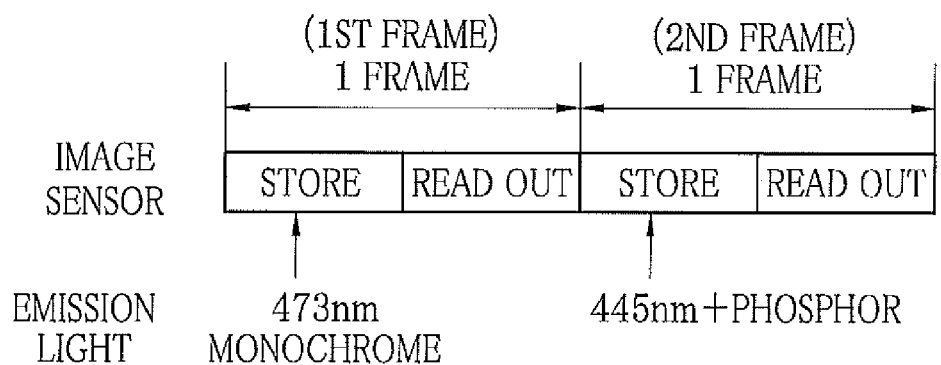
FIG. 6B is an explanatory view illustrating imaging control of the image sensor in a biological functional information observation mode.

On the other hand, in the biological functional information observation mode as shown in FIG. 6B, two steps, a step for storing the charge obtained by the photoelectric conversion of the oxygen saturation measuring beams (the narrowband light of 473 nm) and a step for reading out the stored charge, are performed in a single frame period (first frame). Then, two steps, a step for storing the charge obtained by the photoelectric conversion of the white light (445 nm+MW) and a step for reading out the stored charge, are performed in a single frame period (second frame). The imaging control of the two frames is repeated in the biological functional information observation mode.

Note that the image signal of the first frame is composed of a blue signal B1 outputted from the B pixel of the image sensor 60, a green signal G1 outputted from the G pixel of the image sensor 60, and a red signal R1 outputted from the R pixel of the image sensor 60. The image signal of the second frame is the same as the image signal obtained in the normal light observation mode. The image signal of the second frame is composed of a blue signal B2 outputted from the B pixel, a green signal G2 outputted from the G pixel, and a red signal R2 outputted from the R pixel.

Note that various channels (not shown) are provided inside the handle section 35 and the scope 32 of the endoscope device 12. The channels include a forceps channel through which a sample collecting device or the like is inserted and an air/water channel.

As shown in FIG. 2, the image processor 73 comprises a normal light image processing section 80 and a functional image processing section 82. The image processor 73 performs predetermined image processing on the image signal from the endoscope device 12. The normal light image processing section 80 performs predetermined image processing on the image signal, obtained in the normal light observation mode, to produce a normal light image.

The functional image processing section 82 calculates information on the blood volume of the observation object and information on the oxygen saturation level of hemoglobin in blood of the observation object, based on the image signal inputted from the endoscope device 12. The functional image processing section 82 produces a blood volume image, in which the calculated blood volume is visualized in pseudo color, and an oxygen saturation image, in which the calculated oxygen saturation level is visualized in pseudo color. The functional image processing section 82 comprises a signal ratio calculator 84, correlation storage 85, a blood volume and an oxygen saturation calculator 86, a blood volume image generator 87, and an oxygen saturation image generator 88.

The signal ratio calculator 84 calculates a signal ratio B1/G2 between the blue signal B1 of the first frame and the green signal G2 of the second frame, and a signal ratio R2/G2 between the green signal G2 of the second frame and the red signal R2 of the second frame, out of the image signals obtained in the biological functional information observation mode. Thereby, the blue signal B1 and the red signal R2 are standardized by the green signal G2. The signal ratios are calculated for each pixel of the image signal. Note that the signal ratios may be calculated for only the pixels of a vascular portion of the image signal. In this case, the vascular portion is determined based on a difference between an image signal of the vascular portion and an image signal of a portion other than the vascular portion.

Figure 7:
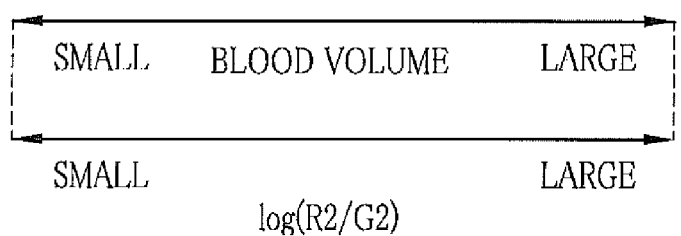
FIG. 7 is a graph illustrating a correlation between blood volume and a signal ratio R2 /G2.

The correlation storage 85 stores a correlation between the signal ratios B1/G2 and R2/G2, the blood volume, and the oxygen saturation level. As shown in FIG. 7, the correlation between the signal ratio and the blood volume is stored in a one-dimensional table which is defined such that the blood volume increases with the signal ratio R2/G2. Note that the signal ratio R2/G2 is represented by a log scale.

Figure 8:
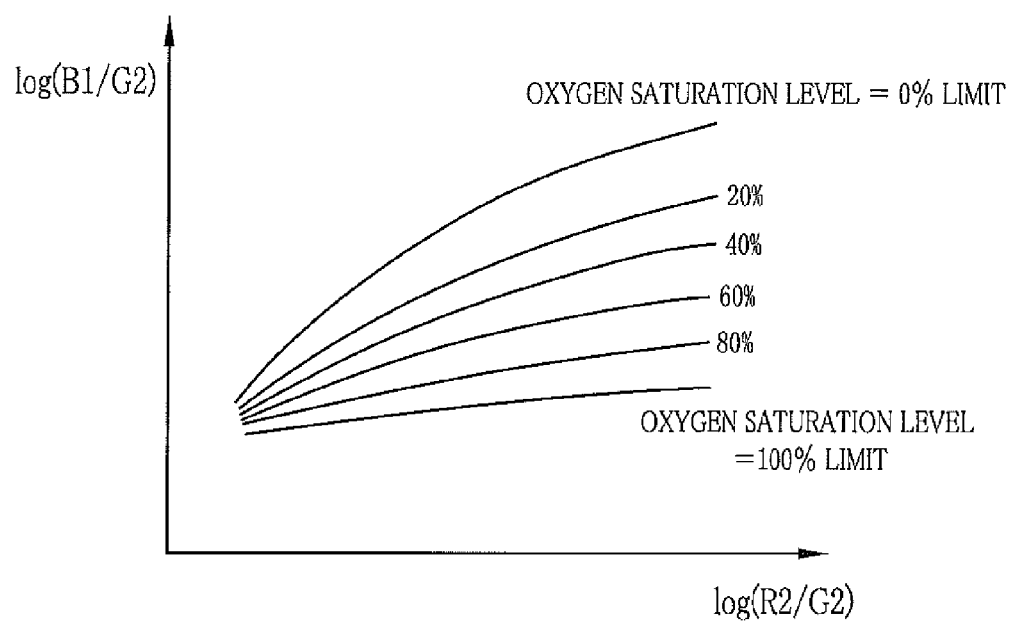
FIG. 8 is a graph illustrating a correlation between an oxygen saturation level and signal ratios B1/G2 and R2/G2.

The correlation between the signal ratios and the oxygen saturation level is stored in a two dimensional table shown in FIG. 8. The two dimensional table defines contour lines of the oxygen saturation levels on a two dimensional space. The positions and shapes of the contour lines are obtained by physical simulation of light scattering, and vary according to the blood volume. For example, a space between the contour lines increases or decreases with a change in the blood volume. Note that the signal ratios B1/G2 and R2/G2 are represented in the log scale.

Figure 9:
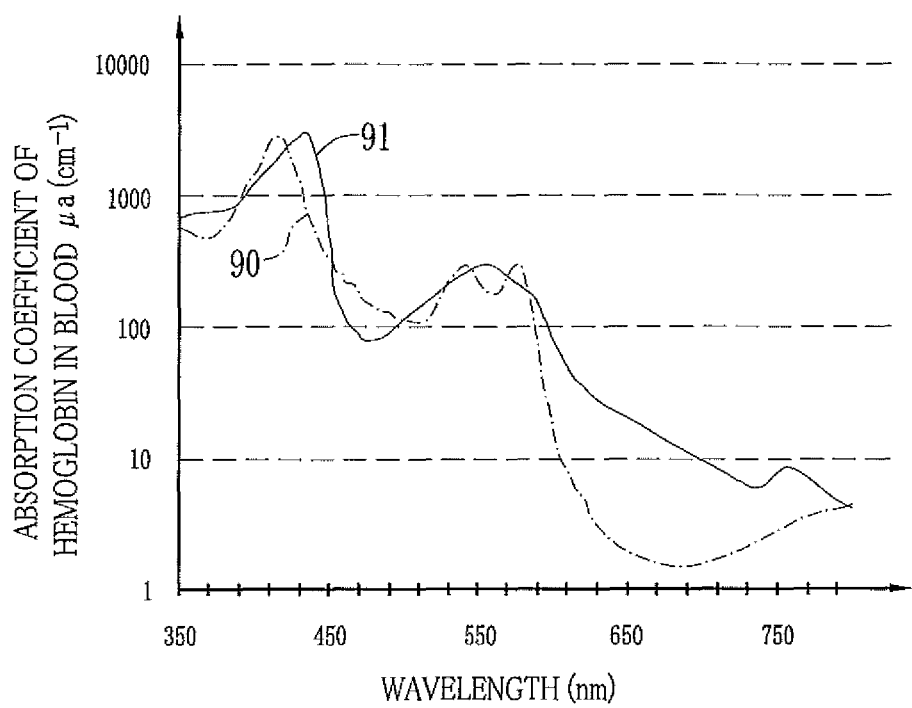
FIG. 9 is a graph illustrating extinction coefficients of hemoglobin.

The above-described correlations are closely related to light absorption properties and light scattering properties of oxyhemoglobin and deoxyhemoglobin shown in FIG. 9. In FIG. 9, a curve 90 represents an extinction coefficient of oxyhemoglobin. A curve 91 represents an extinction coefficient of deoxyhemoglobin. As shown in FIG. 9, it is easy to obtain information on the oxygen saturation level at a wavelength, for example, 473 nm at which a difference between the extinction coefficient of the oxyhemoglobin and the extinction coefficient of the deoxyhemoglobin is large. However, the blue signal containing a signal corresponding to the light of 473 nm is highly dependent on both the oxygen saturation level and the blood volume. Hence, the signal ratios B1/G2 and R2/G2 are used to obtain the blood volume and the oxygen saturation level accurately. The signal ratios B1/G2 and R2/G2 are obtained from the red signal R2 and the green signal G2 in addition to the blue signal B1. The red signal R2 corresponds to the light which varies depending mainly on the blood volume. The green signal G2 is used to standardize the blue signal B1 and the red signal R2.

The following three observations are obtained from wavelength dependence of the extinction coefficient of hemoglobin in blood.

1. In a wavelength range close to 470 nm, for example, in a blue wavelength range with the center wavelength of 470 nm±10 nm, the extinction coefficient varies significantly in accordance with a change in the oxygen saturation level.
2. When averaged in a green wavelength range from 540 nm to 580 nm, the extinction coefficient is likely to be unaffected by the oxygen saturation level.
3. In a red wavelength range from 590 nm to 700 nm, the extinction coefficient appears to vary significantly in accordance with a change in the oxygen saturation level. Actually, however, the extinction coefficient is likely to be unaffected by the oxygen saturation level because the value of the extinction coefficient is extremely small.

The light in a wavelength range from 470 to 700 nm has the following characteristics: a scattering coefficient in mucosal tissue is small; the wavelength dependence is small. By using the light in this wavelength range as the illumination light, blood information is obtained while influence of the blood depth is reduced. The blood information includes information on blood volume and information on oxygen saturation level.

The blood volume and the oxygen saturation calculator 86 calculates both the blood volume and the oxygen saturation level in each pixel with the use of the correlations stored in the correlation storage 85 and the signal ratios B1/G2 and R2/G2 obtained by the signal ratio calculator 84. Here, a method for calculating the blood volume and the oxygen saturation level in each of cases 1 and 2 is described. In the case 1, signal ratios B1*/G2* and R2*/G2* are obtained. In the case 2, the signal ratio B1*/G2*, which is the same as that obtained in the case1, and a signal ratio R2/G2, which differs from the signal ratio R2*/G2* in the case 1, are obtained.

First, the case 1 (B1*/G2*, R2*/G2*) is described. A blood volume H1 corresponding to the signal ratio R2*/G2* is obtained from the correlation illustrated in FIG. 10A. Then, an oxygen saturation level corresponding to the blood volume H1 is obtained, out of the oxygen saturation levels (0% to approximately 80%) indicated by the signal ratio B1*/G2*, from the correlation illustrated in FIG. 10B. The obtained oxygen saturation level is 60%.

Figure 10A:
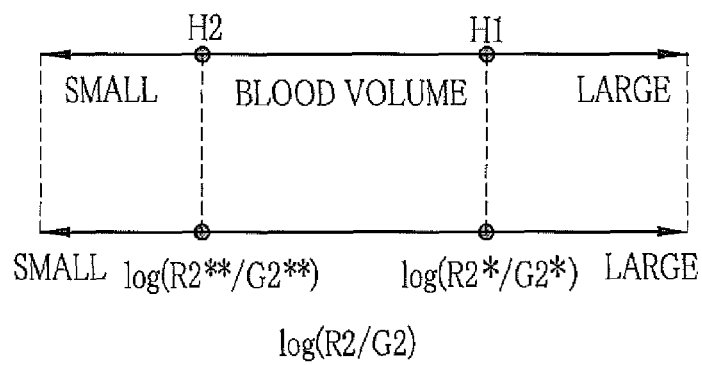
FIG. 10A is an explanatory view illustrating a method for obtaining a blood volume from a signal ratio with the use of the graph in FIG. 7.

Next, the case 2 (B1*/G2*, R2/G2) is described. A blood volume H2 corresponding to the signal ratio R2/G2 is obtained as illustrated in FIG. 10A. The blood volume H2 is smaller than the blood volume H1 of the case 1. Then, an oxygen saturation level corresponding to the blood volume H2 is obtained, out of the oxygen saturation levels (0% to approximately 80%) indicated by the signal ratio B1*/G2*, from the correlation illustrated in FIG. 10B in a manner similar to the case 1. The obtained oxygen saturation level is 20%, which is much less than that of the case 1.

As described above, the signal ration B1*/G2* includes a wavelength component in which the extinction coefficient of the oxyhemoglobin differs from that of the deoxyhemoglobin. The signal ratio B1*/G2* contains a considerable amount of information related to the oxygen saturation level. However, the signal ratio B1*/G2* is also dependent on the blood volume. Hence, the signal ratio B1*/G2* fluctuates significantly in a range from 0% to 80%. For example, although the cases 1and 2 have the same signal ratio B1*/G2*, the difference in the oxygen saturation level reaches 40% due to the difference in the blood volume. Namely, the value of the oxygen saturation level indicated by the signal ratio B1*/G2* is not accurate because the signal ratio B1*/G2* includes information on both the blood volume and the oxygen saturation level. In the present invention, first, the blood volume is obtained from the signal ratio R2/G2. Then the oxygen saturation level corresponding to the blood volume is obtained out of the oxygen saturation levels indicated by the signal ratio B1/G2. Thereby the oxygen saturation level not dependent on the blood volume is calculated.

Figure 10B:
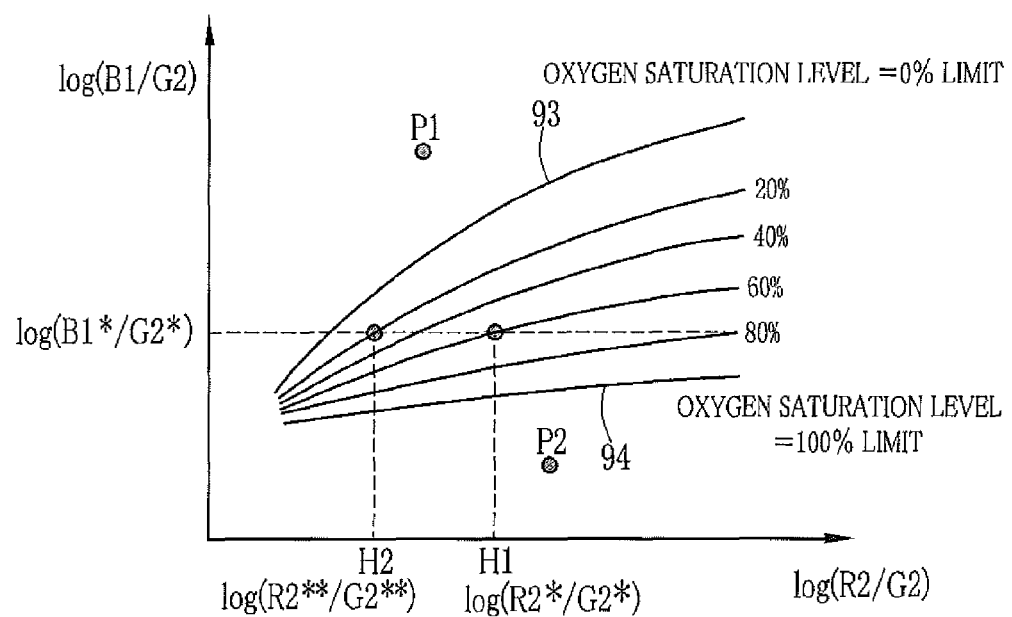
FIG. 10B is an explanatory view illustrating a method for obtaining an oxygen saturation level from a signal ratio with the use of the graph in FIG. 8.

Note that, as shown in FIG. 10B, the oxygen saturation level is 0% in a case where a point P1 corresponding to the signal ratios B1/G2 and B1/G2 is located above a lower limit line 93. The oxygen saturation level is 100% in a case where a point P2 is located below an upper limit line 94. Note that, if a point is not located between the lower and the upper limit lines 93 and 94, the oxygen saturation level of the pixel may not be displayed.

The blood volume image generator 87 produces a blood volume image which shows the blood volume, calculated by the blood volume and the oxygen saturation calculator 86, in pseudo-color. The blood volume image is composed of a video signal comprising luminance Y and color difference signals Cb and Cr. The green signal G2 is assigned to the luminance Y. The green signal G2 corresponds to the reflected light in a wavelength range in which the light absorption by the hemoglobin is relatively high. Hence, the image produced based on the green signal G2 allows visible observation of surface unevenness of mucosa, blood vessels, and the like. Thus, overall brightness of the pseudo color image is defined by assigning the green signal G2 to the luminance.

Figure 11:
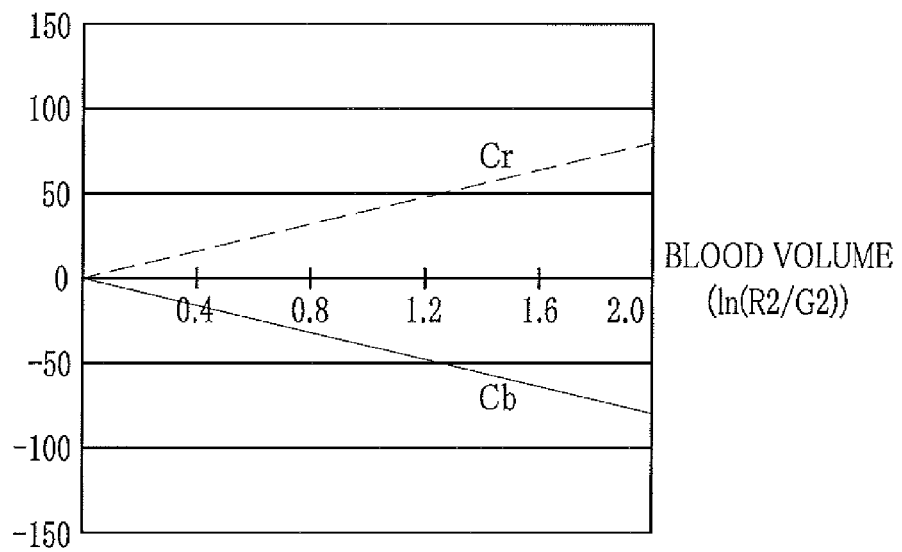
FIG. 11 is a graph illustrating a relation between blood volume and color difference signals.

According to a color table 87a, signal values corresponding to the blood volume are assigned to the color difference signals Cb and Cr. As shown in FIG. 11, in the color table 87a, the signal value of the color difference signal Cb is defined to decrease as the blood volume increases. The signal value of the color difference signal Cr is defined to increase as the blood volume increases. Hence, redness of the blood volume image increases as the blood volume increases. The redness decreases in chroma and becomes closer to monochromatic as the blood volume decreases. Note that the color table 87a also shows a relation between the signal ratio B1/G2 and the color difference signals Cb and Cr, so that the blood volume image may be produced based on the signal ratio R2/G2, without calculation of the blood volume.

The oxygen saturation image generator 88 produces the oxygen saturation image which shows the oxygen saturation level, obtained by the blood volume and the oxygen saturation calculator 86, in the pseudo color. The oxygen saturation image is composed of a video signal comprising luminance Y and color difference signals Cb and Cr, in a manner similar to the blood volume image. The green signal G2 is assigned to the luminance Y. According to a color table 88a, signal values corresponding to the oxygen saturation level are assigned to the color difference signals Cb and Cr, respectively.

Figure 12:
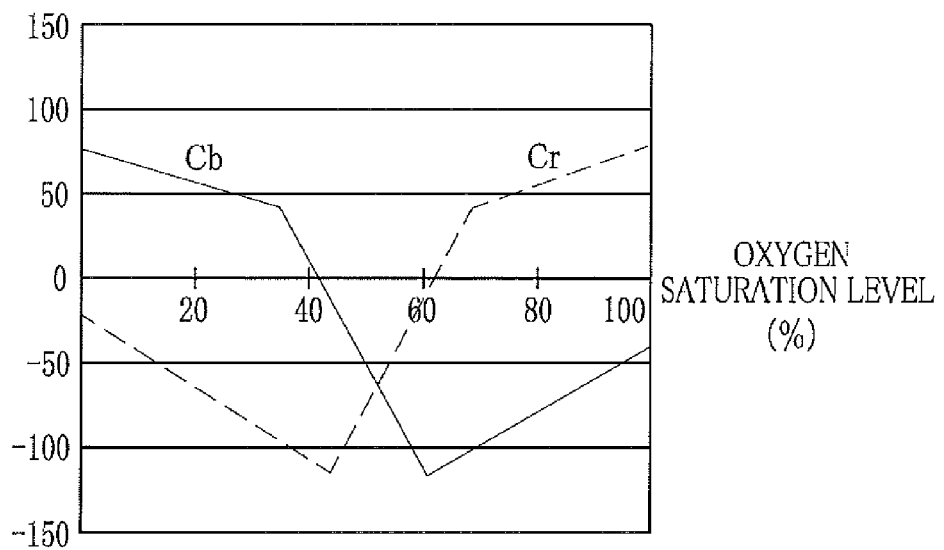
FIG. 12 is a graph illustrating a relation between oxygen saturation level and the color difference signals.

As shown in FIG. 12, a signal value of the color difference signal Cr is defined to be positive, while a signal value of the color difference signal Cb is defined to be negative in the color table 88a in a case where the oxygen saturation level is high. In a case where the oxygen saturation level is low, on the other hand, the signal value of the color difference signal Cr is defined to be negative, while the signal value of the color difference signal Cb is defined to be positive. In a case where the oxygen saturation level is at a medium level, the signal values are defined such that a relationship in magnitude between the signal value of the color difference signal Cr and the signal value of the color difference signal Cb is reversed. Hence, the color of the oxygen saturation image changes from blue to light blue to green to yellow to orange to red as the oxygen saturation level increases.

Figure 13:
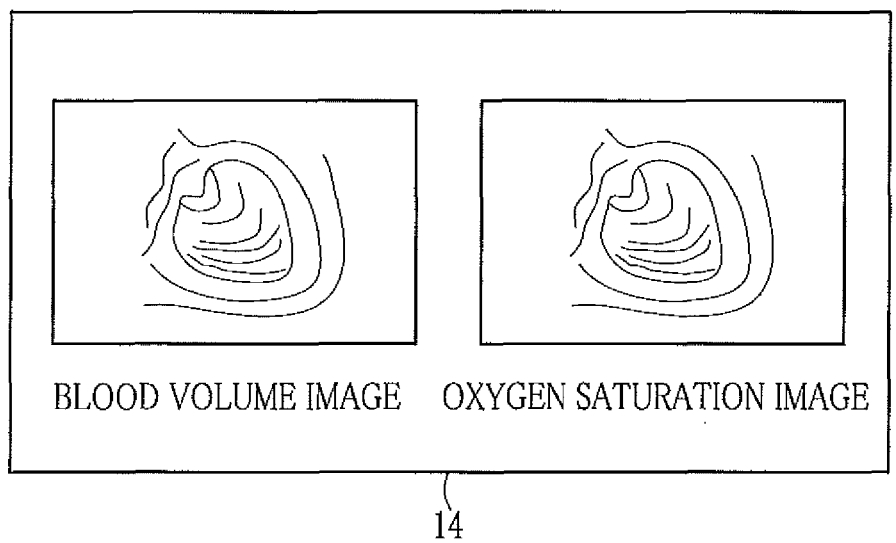
FIG. 13 is a diagram of a screen of a display device displaying a blood volume image and an oxygen saturation image side by side.
Figure 14:
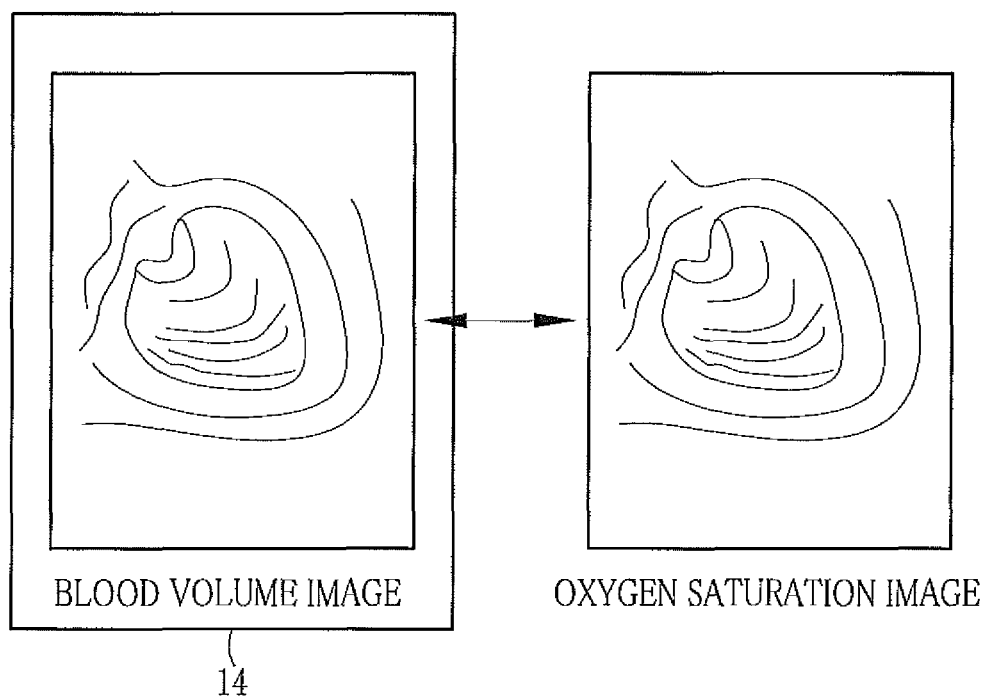
FIG. 14 is a diagram of a screen of the display device displaying one of the blood volume image and the oxygen saturation image.

The blood volume image and the oxygen saturation image thus produced are displayed on the display device 14. As shown in FIG. 13, the sizes of the oxygen saturation image and the blood volume image may be reduced and the reduced images may be displayed side by side at a time. Alternatively, as shown in FIG. 14, a user may operate an image selecting means (not shown), provided in the input device 15, to choose one of the oxygen saturation image and the blood volume image. The chosen image is displayed on the display device 14. Thus, endoscopic diagnosing is performed using both the blood volume image and the oxygen saturation image. Hence, the capability to diagnose a lesion, such as undifferentiated early gastric cancer characterized by both the oxygen saturation level and the blood volume, is improved.

Figure 15:
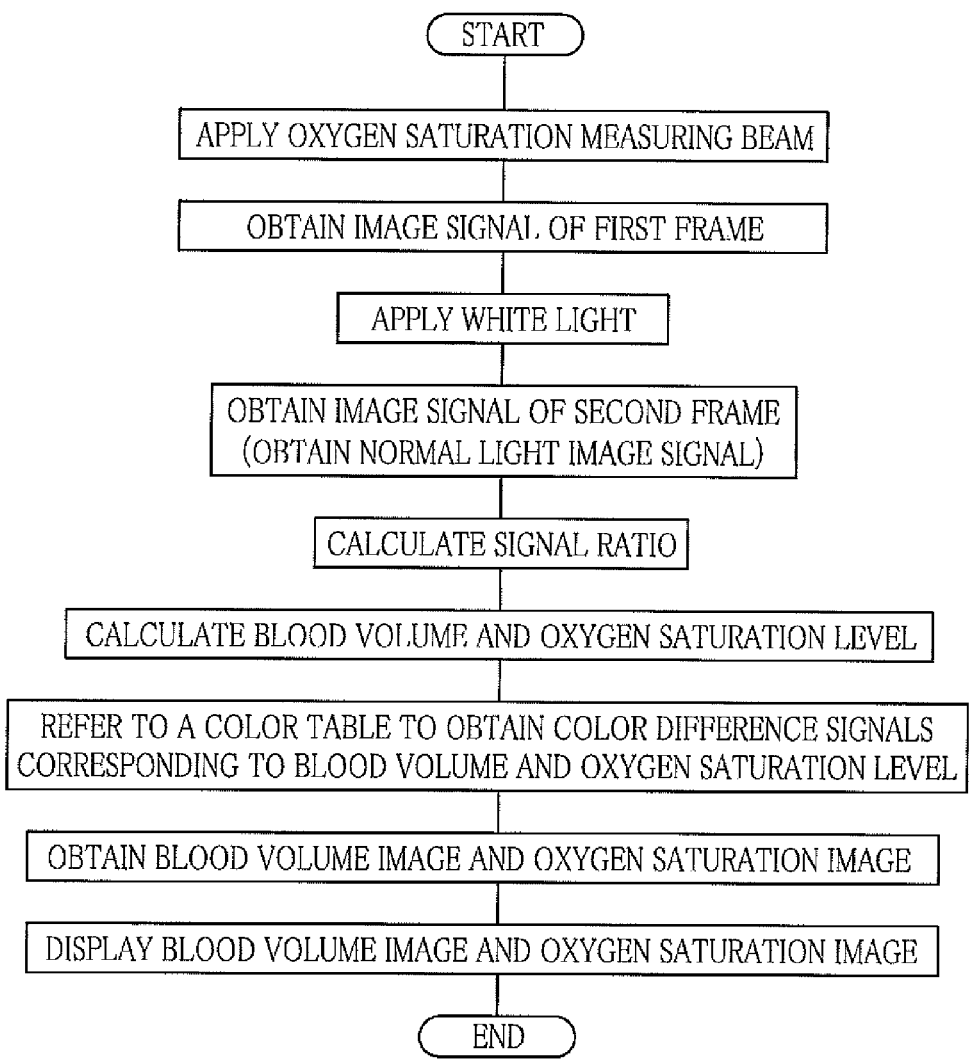
FIG. 15 is a flowchart illustrating an operation of the present invention.
Figure 16:
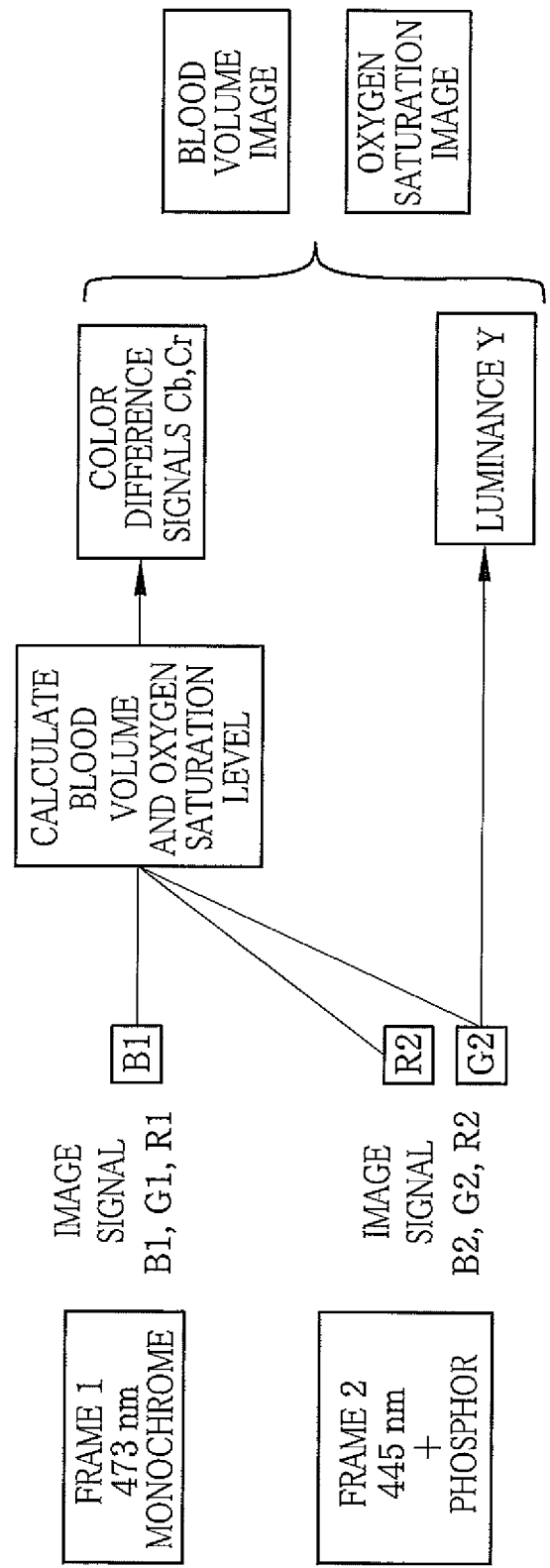
FIG. 16 is a block diagram illustrating steps for producing a blood volume image and an oxygen saturation image.

Next, an operation of the present invention is described with reference to a flowchart in FIG. 15 and a block diagram in FIG. 16. Note that the scope 32 is inserted in a body cavity, for example, a digestive tract, in the normal light observation mode. With the operation of the angle knob 35a, the scope distal portion 40 is set to observe a desired observation object. Thereby the normal light observation is performed. In the normal light observation, a color normal light image of the observation object illuminated with the white light is displayed on the display device 14.

In a case where the observation object is assumed to be a lesion, the selection switch 17 of the endoscope device is operated to switch the observation mode to the biological functional information observation mode. When the observation mode is switched to the biological functional information observation mode, the oxygen saturation measuring beams which are narrowband light beams having the center wavelength of 473 nm are applied from the scope distal portion 40 to the observation object. The reflection light from the observation object and the like is captured by the image sensor 60. The image sensor 60 is a color CCD composed of B pixels, G pixels, and R pixels. Thereby, an image signal of a first frame is obtained. The image signal of the first frame is composed of a blue signal B1, a green signal G1, and a red signal R1.

After the image signal of the first frame is obtained, the white light, generated by the excitation light with the center wavelength of 445 nm, is applied to the observation object through the scope distal portion 40. The reflection light from the observation object is captured by the image sensor 60. Thereby, an image signal (normal light image signal) of a second frame is obtained. The image signal of the second frame is composed of a blue signal B2, a green signal G2, and a red signal R2.

After the image signal of the second frame is obtained, the signal ratio calculator 84 obtains the signal ratios B1/G2 and R2/G2. After the signal ratios are obtained, the blood volume and the oxygen saturation calculator 86 obtains the blood volume and the oxygen saturation level, based on the correlations stored in the correlation storage 85. The blood volume corresponds to the signal ratio B1/G2 obtained by the signal ratio calculator 84. The oxygen saturation level corresponds to the signal ratios B1/G2 and B1/G2 obtained by the signal ratio calculator 84. The blood volume and the oxygen saturation level are obtained for every pixel.

After the blood volume and the oxygen saturation level are obtained for each pixel, the color table 87a in the blood volume image generator 87 is referred to. Thereby, the color difference signals Cb and Cr corresponding to the blood volume are obtained. The blood volume image is produced based on the obtained color difference signals Cb and Cr and the luminance Y to which the green signal G2 is assigned. The blood volume image shows the blood volume in pseudo color. The oxygen saturation image is produced using the color table 88a in a similar manner. The oxygen saturation image shows the oxygen saturation level in pseudo color. The produced blood volume image and the produced oxygen saturation image are displayed on the display device 14.

Figure 17:
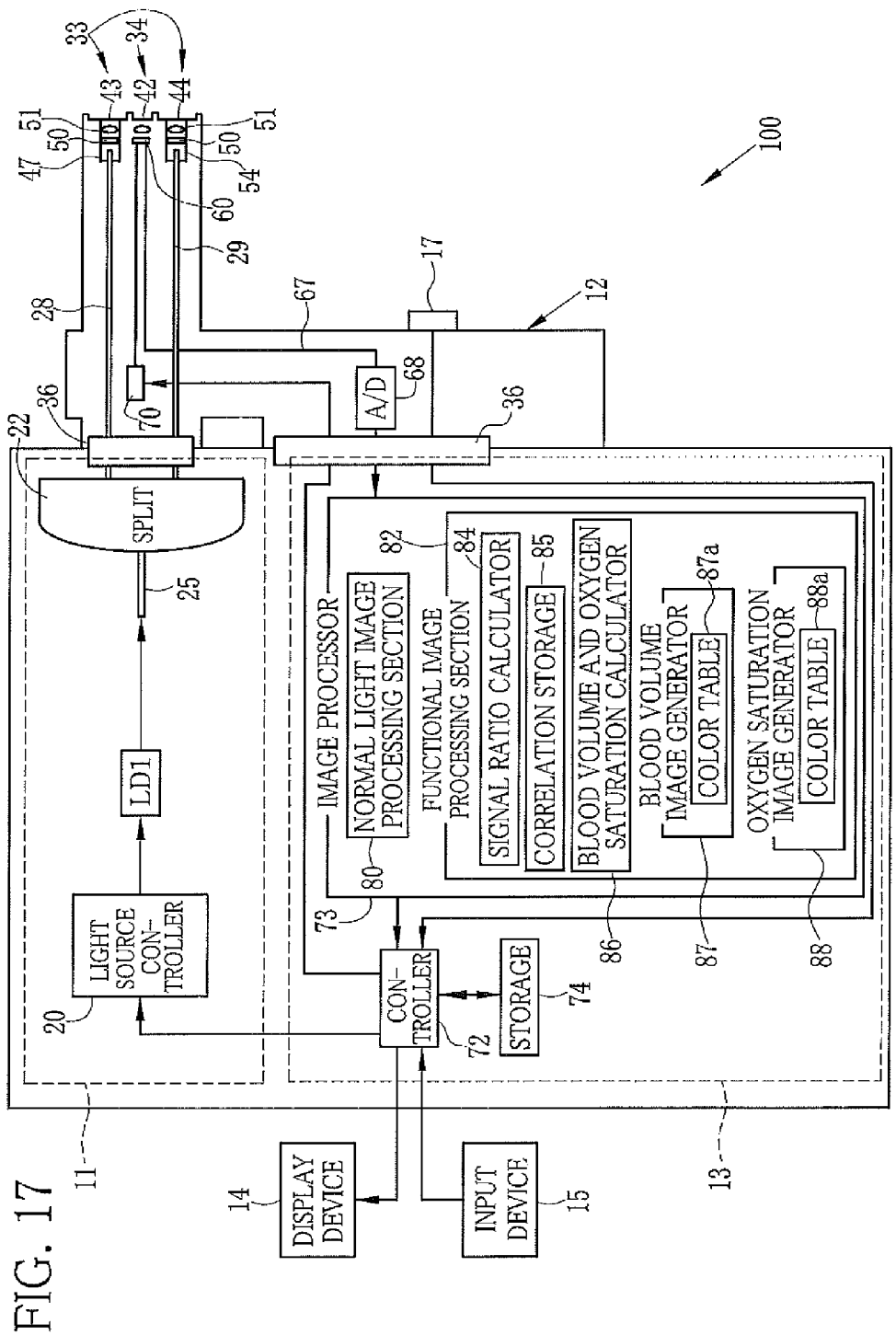
FIG. 17 is a block diagram illustrating an outline of an endoscope system of a second embodiment.

Note that, in the first embodiment, the blood volume and the oxygen saturation level are calculated using the two frames of image signals. The image signal of the first frame is obtained by applying the narrowband light having the center wavelength of 473 nm. The image signal of the second frame is obtained by applying the white light. The white light is emitted from the phosphor excited by the excitation light having the center wavelength of 445 nm. Alternatively, as will be described in a second embodiment illustrated in FIG. 17, the blood volume and the oxygen saturation level may be obtained from an image signal of a single frame. The image signal of the single frame is obtained by capturing an image of the observation object illuminated with the white light. The white light is emitted from the phosphor 50 excited by the excitation light having the center wavelength of 473 nm from the laser light source LD1. Note that, unlike the endoscope system 10 applying the four paths of light beams from the four respective projection units 46, 47, 53, and 54, an endoscope system 100 applies two paths of light beams from the two respective projection units 47 and 54.

In the image signal, the blue signal B includes a signal corresponding to the excitation light having the center wavelength of 473 nm and a signal corresponding to a small amount of light out of the light from the phosphor being excited. The green signal G includes a signal corresponding to spectral illumination in a wavelength range mainly from 540 nm to 580 nm out of the light from the phosphor being excited. The red signal R includes a signal corresponding to a small amount of the excitation light and a signal corresponding to spectral illumination in the wavelength range from 590 nm to 700 nm out of the light from the phosphor being excited.

Hence, the signal ratio used for the calculation of the blood volume is R/G. The signal ratios used for the calculation of the oxygen saturation level are B/G and R/G. The signal ratio R/G corresponds to the above-described signal ratio R2/G2. The signal ratio B/G corresponds to the above-described signal ratio B1/G2. Methods for calculating the blood volume and the oxygen saturation level are similar to the above, so that descriptions thereof are omitted. Note that the green signal G is assigned to the luminance to produce the pseudo-color blood volume image and the pseudo-color oxygen saturation image.

Figure 18:
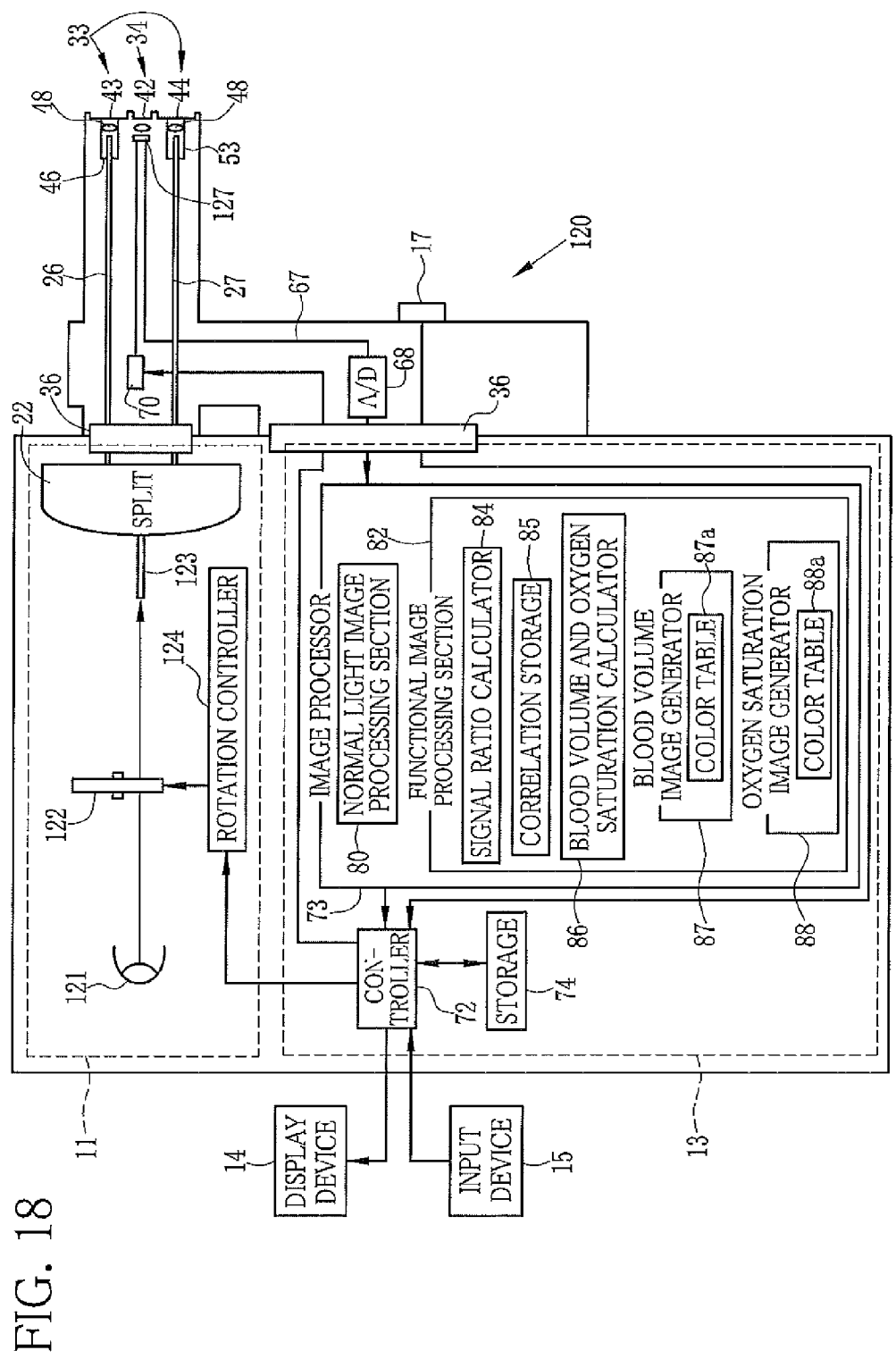
FIG. 18 is a block diagram illustrating an outline of an endoscope system of a third embodiment.
Figure 19:
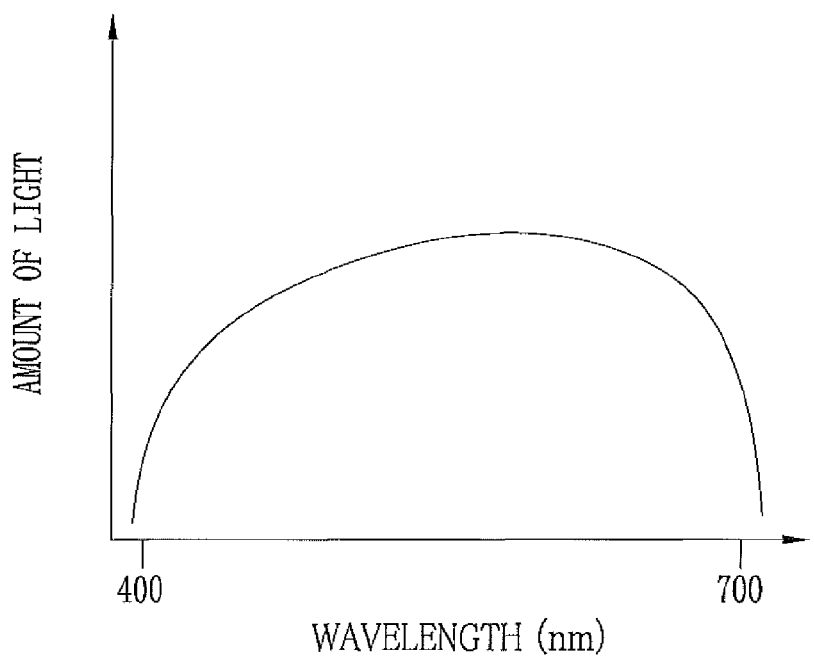
FIG. 19 is a graph representing an emission spectrum of the white light.

As shown in FIG. 18, an endoscope system 120 of a third embodiment employs the light source device 11 of a rotating-filter type. Hence, the endoscope system 120 is provided with a broadband light source 121, a rotation filter 122, an optical fiber 123, and a rotation controller 124, instead of the laser light sources LD1 and LD2, the light source controller 20, and the combiner 21 used in the first and second embodiments. The broadband light source 121 (for example, a xenon lamp or the like) emits white light having spectral intensity shown in FIG. 19. The rotation filter 122 transmits a wavelength component of the oxygen saturation measuring light, out of the white light, or the whole of the white light. The light transmitted through the rotation filter 122 is incident on the optical fiber 123. The rotation controller 124 controls the rotation of the rotation filter 122.

The light incident on the optical fiber 123 is split into the two paths of light by the splitter 22. One of the two paths of the light is applied from the projection unit 46 to the observation object through the light guide 26. The other path of the light is applied from the projection unit 53 to the observation object through the light guide 27. Note that parts of the endoscope system 120 other than the above have a configuration similar to that of the endoscope system 10 shown in FIG. 2, so that descriptions thereof are omitted.

Figure 20:
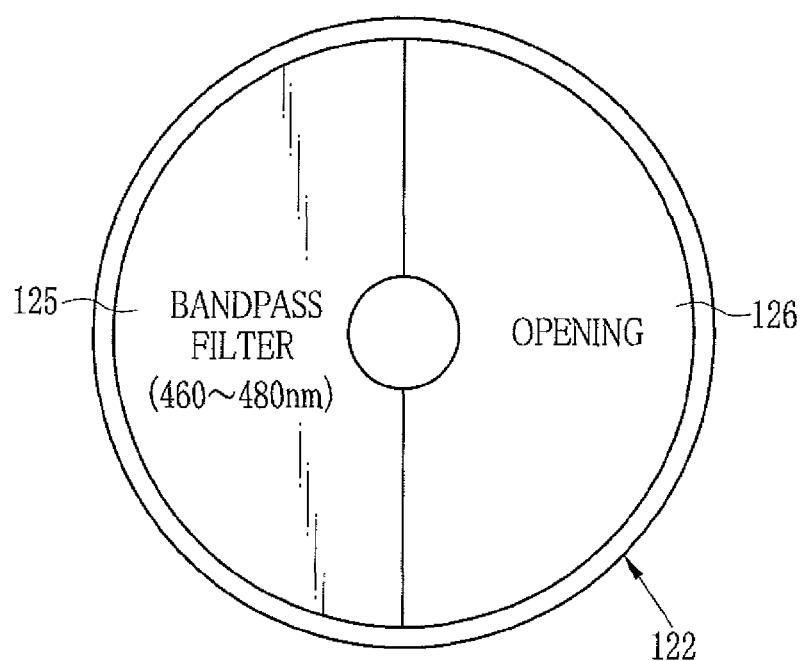
FIG. 20 is a front view of a rotation filter.

As shown in FIG. 20, the rotation filter 122 is composed of a bandpass filter 125 and an opening 126. The bandpass filter 125 transmits the oxygen saturation measuring light (see FIG. 4) in a wavelength range from 460 nm to 480 nm out of the white light. The opening 126 allows the whole of white light to pass therethrough. By rotating the rotation filter 122, the oxygen saturation measuring light and the white light is applied alternately to the observation object. Similar to the first embodiment, the image signals B1, G1, R1 of the first frame are obtained with the application of the oxygen saturation measuring light. The image signals B2, G2, and R2 of the second frame are obtained with the application of the white light. The oxygen saturation image is produced from the obtained two frames of image signals in a manner similar to the first embodiment.

In the third embodiment, in the first frame, the blue signal B1 includes a signal corresponding to light in the wavelength range from 460 nm to 480 nm. In the second frame, the blue signal B2 includes a signal corresponding to light in a wavelength range from 400 nm to 530 nm. The green signal G2 includes a signal corresponding to light in the wavelength range from 540 nm to 580 nm. The red signal R2 includes a signal corresponding to light in the wavelength range from 590 nm to 700 nm. Note that methods for calculating the blood volume and the oxygen saturation level are similar to those of the first embodiment, so that descriptions thereof are omitted.

Figure 21:
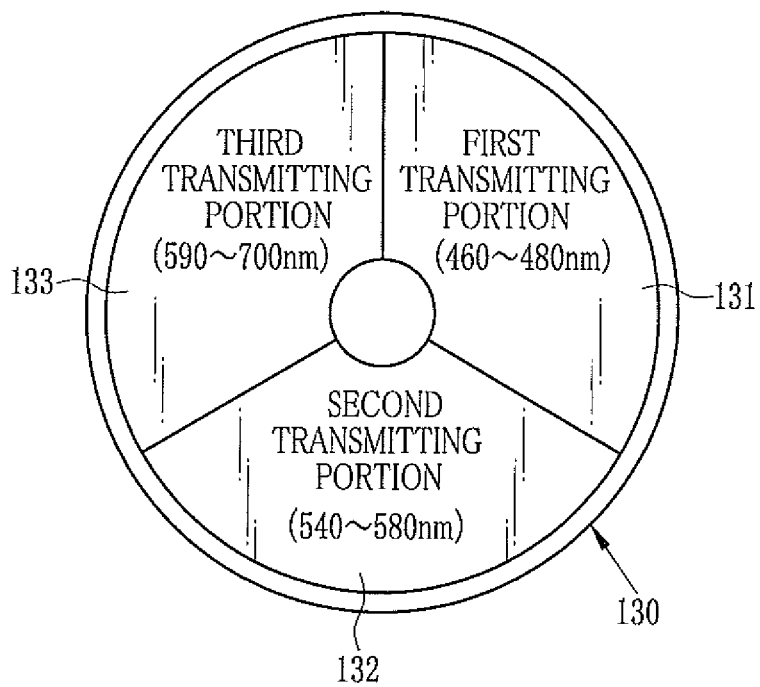
FIG. 21 is a front view of a rotation filter having transmission characteristics which differ from those of the rotation filter of FIG. 20.

Note that, in the third embodiment, a rotation filter 130 shown in FIG. 21 may be used instead of the rotation filter 122 shown in FIG. 20. A first transmitting portion 131 of the rotation filter 130 transmits first transmission light in the wavelength range from 460 nm to 480 nm out of the white light from the broadband light source 121. A second transmitting portion 132 transmits second transmission light in the wavelength range from 540 to 580 nm out of the white light. A third transmitting portion 133 transmits third transmission light in the wavelength range from 590 nm to 700 nm out of the white light. The first to third transmission light is applied to the observation object sequentially as the rotation filter 130 rotates.

In the case where the rotation filter 130 is used, a monochrome image sensor 127 captures an image every time one of the transmission light is applied. Hence, image signals of three frames are obtained by applications of first to third transmission light, respectively. The image signal obtained by the application of the first transmission light is the blue signal B. The image signal obtained by the application of the second transmission light is the green signal G. The image signal obtained by the application of the third transmission light is the red signal R.

Hence, the signal ratio used for the calculation of the blood volume is R/G. The signal ratios used for the calculation of the oxygen saturation level are B/G and R/G. The signal ratio R/G corresponds to the signal ratio B1/G2 of the first embodiment. The signal ratio B/G corresponds to the signal ratio B1/G2 of the first embodiment. The methods for calculating the blood volume and the oxygen saturation level are similar to those of the first embodiment, so that descriptions thereof are omitted. Note that the green signal G is assigned to the luminance to produce the pseudo-color blood volume image and the pseudo-color oxygen saturation image.

Figure 22:
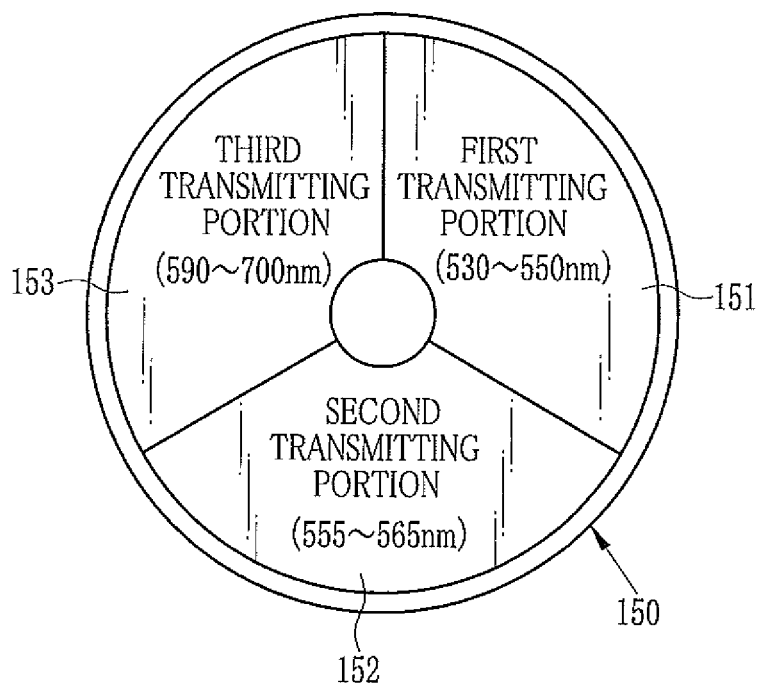
FIG. 22 is a front view of a rotation filter having transmission characteristics which differ from those of the rotation filters of FIGS. 20 and 21.

In the third embodiment, note that a rotation filter 150 shown in FIG. 22 may be used instead of the rotation filter 130 shown in FIG. 21. Transmittance of each transmitting portion of the rotation filter 150 differs from that of the rotation filter 130. A first transmitting portion 151 of the rotation filter 150 transmits first transmission light in a wavelength range from 530 nm to 550 nm. A second transmitting portion 152 transmits second transmission light in a wavelength range from 555 nm to 565 nm. A third transmitting portion 153 transmits third transmission light in the wavelength range from 590 nm to 700 nm. The first to third transmission light is applied sequentially to the observation object as the rotation filter 150 rotates.

In the case where the rotation filter 150 is used, the image sensor 127 captures an image every time one of the transmission light is applied. The G pixels of the image sensor 60 are mainly sensitive to the first and second transmission light, so that green signals Ga and Gb are obtained as the image signals when the first and second transmission light is applied. The R pixels of the image sensor 60 are mainly sensitive to the third transmission light, so that a red signal Rc is obtained as the image signal by the application of the third transmission light. Here, the Ga and the Rc are the image signals which correspond to the reflection light of the two respective wavelength ranges in each of which the extinction coefficient varies in accordance with an oxygen saturation level of hemoglobin in blood. The Gb is the image signal which corresponds to the reflection light of the single wavelength range in which the extinction coefficient does not vary. Hence, the Ga/Gb varies depending on the oxygen saturation level and the blood volume. The Rc/Gb varies depending mainly on the blood volume.

Hence, the signal ratio Rc/Gb is used to calculate the blood volume. The signal ratios Ga/Gb and Rc/Gb are used to calculate the oxygen saturation level. The signal ratio Rc/Gb corresponds to the signal ratio B1/G2 of the first embodiment. The signal ratio Ga/Gb corresponds to the signal ratio B1/G2 of the first embodiment. The methods for calculating the blood volume and the oxygen saturation level are similar to those in the first embodiment, so that descriptions thereof are omitted. Note that the green signal Ga or Gb is assigned to the luminance to produce the pseudo-color blood volume image and the pseudo-color oxygen saturation image.

Figure 23:
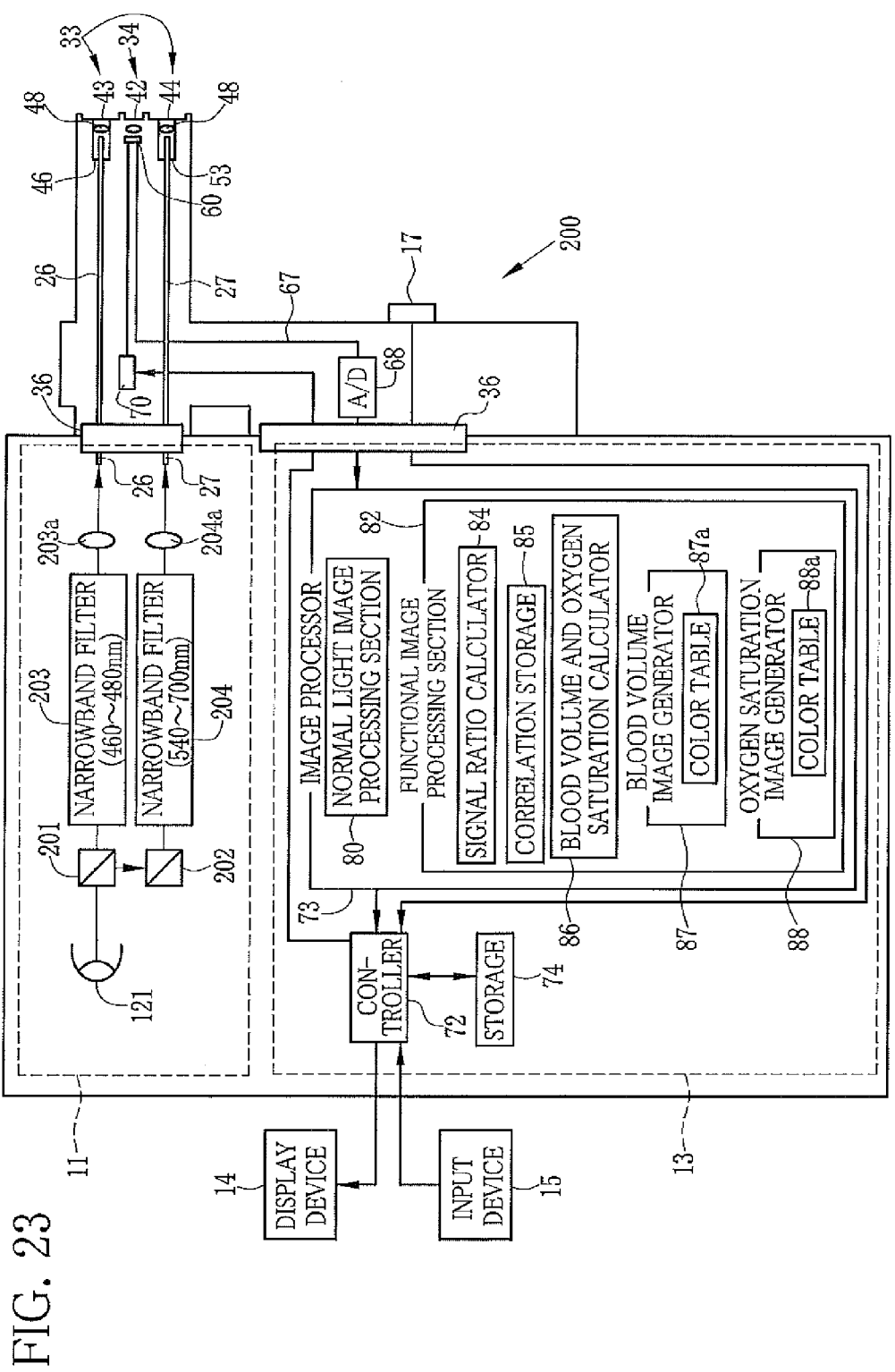
FIG. 23 is a block diagram illustrating a configuration of an endoscope system of a fourth embodiment.

As shown in FIG. 23, instead of the rotation filter 122 shown in the third embodiment, an endoscope system 200 of a fourth embodiment uses a half mirror 201, a reflection mirror 202, and narrowband filters 203 and 204 to generate the light used for calculating the blood volume and the oxygen saturation level. The color image sensor 60 is used to image the inside of the subject. A configuration of other parts of the endoscope system 200 is similar to that of the endoscope system 120 of the third embodiment.

In the light source device 11, the half mirror 201 splits the white light, emitted from the broadband light source 121, into two paths of white light. One of the two paths of white light is incident on the narrowband filter 203. The other path of white light is reflected by the reflection mirror 202 and then incident on the narrowband filter 204. The narrowband filter 203 transmits the light in a wavelength range from 460 nm to 480 nm out of the white light. The narrowband filter 204 transmits the light in a wavelength range from 540 nm to 700 nm out of the white light. The light passed through the narrowband filter 203 is applied to the observation object through a lens 203a and the light guide 26. The light passed through the narrowband filter 204 is applied to the observation object through a lens 204a and the light guide 27. The light passed through the narrowband filters 203 and 204 is applied simultaneously to the observation object.

Hence, in the image signal obtained by the image capture, a signal corresponding the light of 460 to 480 nm is included in the blue signal B. A signal corresponding to the light of 540 to 580 nm is included in the green signal G. A signal corresponding to the light of 590 to 700 nm is included in the red signal R.

Hence, the signal ratio R/G is used to calculate the blood volume. The signal ratios B/G and R/G are used to calculate the oxygen saturation level. The signal ratio R/G corresponds to the signal ratio B1/G2 of the first embodiment. The signal ratio B/G corresponds to the signal ratio B1/G2 of the first embodiment. Methods for calculating the blood volume and the oxygen saturation level are similar to those of the first embodiment, so that descriptions thereof are omitted. Note that the green signal G is assigned to the luminance to produce the pseudo-color blood volume image and the pseudo-color oxygen saturation image.

In the above embodiments, the information related to the blood volume is visualized in pseudo color to produce the blood volume image. The information related to the oxygen saturation level is visualized in pseudo-color to produce the oxygen saturation image. Note that, alternatively, the information related to the blood volume and the oxygen saturation level may be visualized as monochrome images (with gradation between black and white in monochrome).

In the above embodiment, each of the blue signal B1 and the red signal R2 is divided by the green signal G2 to standardize the blue signal B1 and the red signal R2. The blue signal B1 contains a wavelength component in which the extinction coefficient varies in accordance with the oxygen saturation level of hemoglobin in blood. The red signal R2 contains a wavelength component in which the extinction coefficient varies in accordance with the blood volume representing an amount of hemoglobin in blood. Note that the standardization of the blue signal B1 and the red signal R2 is not limited to the above.

Figure 24:
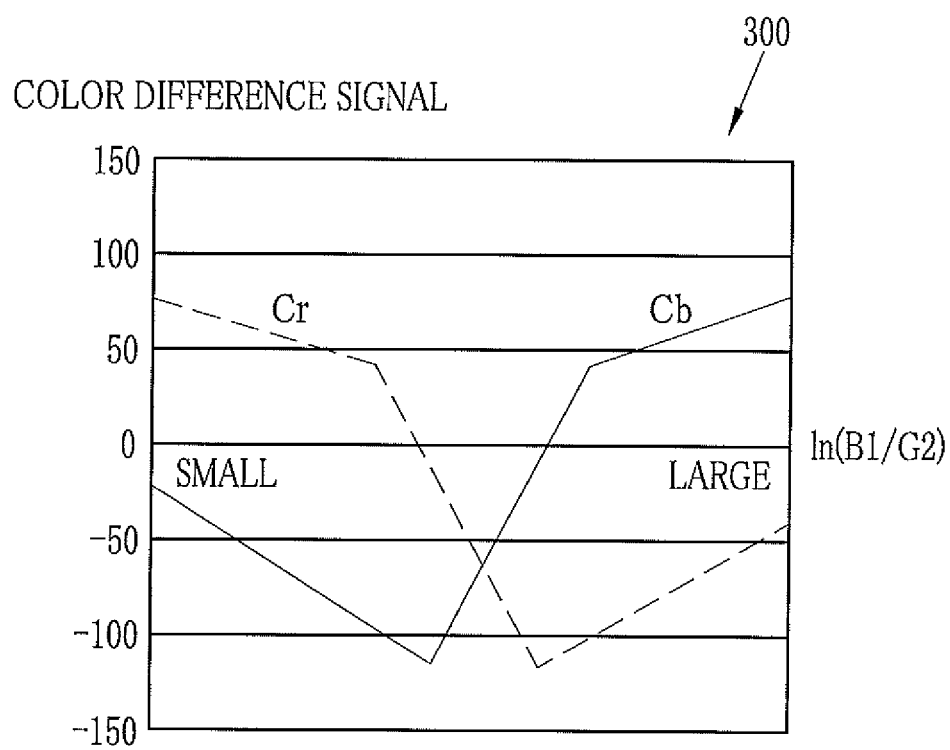
FIG. 24 is a color table illustrating a relation between the signal ratio B1/G2 and the color difference signals.

In the above embodiments, the oxygen saturation level is calculated from the signal ratios B1/G2 and B1/G2 with the use of the correlation stored in the correlation storage 85. The oxygen saturation image is produced based on the oxygen saturation level calculated. Note that the oxygen saturation image may be produced based on the signal ratio B1/G2, without calculating the oxygen saturation level. In this case, the oxygen saturation image is produced using a color table 300, in which the signal ratio B1/G2 is associated with the color difference signals Cr and Cb as shown in FIG. 24 (the G2 is assigned to the luminance signal Y in a manner similar to the above embodiments).

Here, "B1" of the signal ratio B1/G2 has a wavelength component (the wavelength component corresponding to the center wavelength 473 nm) in which the extinction coefficient of the oxyhemoglobin is greater than that of the deoxyhemoglobin. Hence, the signal value of the "B1" increases as the oxygen saturation level decreases. On the other hand, the "G2" has a wavelength component (the wavelength component corresponding to 540 to 580 nm) in which a relationship in magnitude between the coefficients of the oxyhemoglobin and the deoxyhemoglobin is reversed frequently. Hence, the signal value of the signal "G2" does not vary with a change in the oxygen saturation level.

Consequently, the signal value of the signal ratio B1/G2, that is, the "B1" divided by the "G2", increases as the oxygen saturation level decreases. In the color table 300 shown in FIG. 24, in order that a color of a blood vessel on the oxygen saturation image changes from "red to orange to yellow to green to pale blue to blue" as the oxygen saturation level decreases, the signal value of the color difference signal Cr is defined to be positive and the signal value of the color difference signal Cb is defined to be negative in a case where the signal ratio B1/G2 is small (high oxygen saturation level). A relationship in magnitude between the signal values of the color difference signals Cr and Cb is reversed in a case where the signal ratio B1/G2 is in a medium level (medium oxygen saturation level). The signal value of the color difference signal Cr is defined to be negative and the signal value of the color difference signal Cb is defined to be positive in a case where the signal ratio B1/G2 is large (low oxygen saturation level).

Figure 25A:
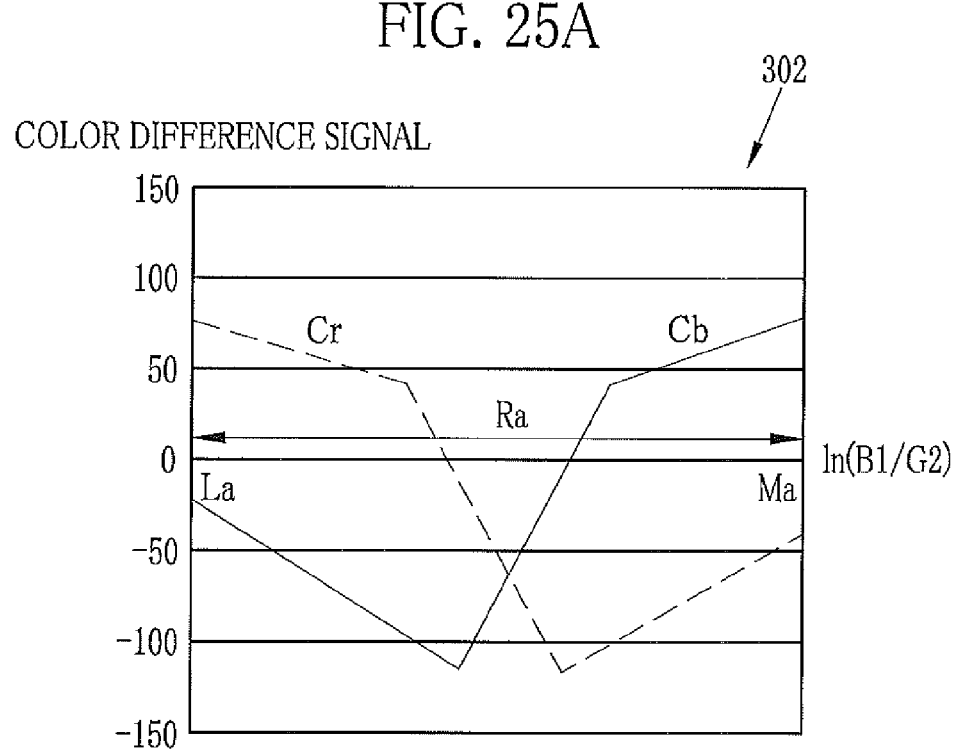
FIG. 25A is a color table illustrating a relation between the signal ratio B1 /G2 and the color difference signals in a case where the signal ratio R2/G2 is greater than or equal to a predetermined value.
Figure 25B:
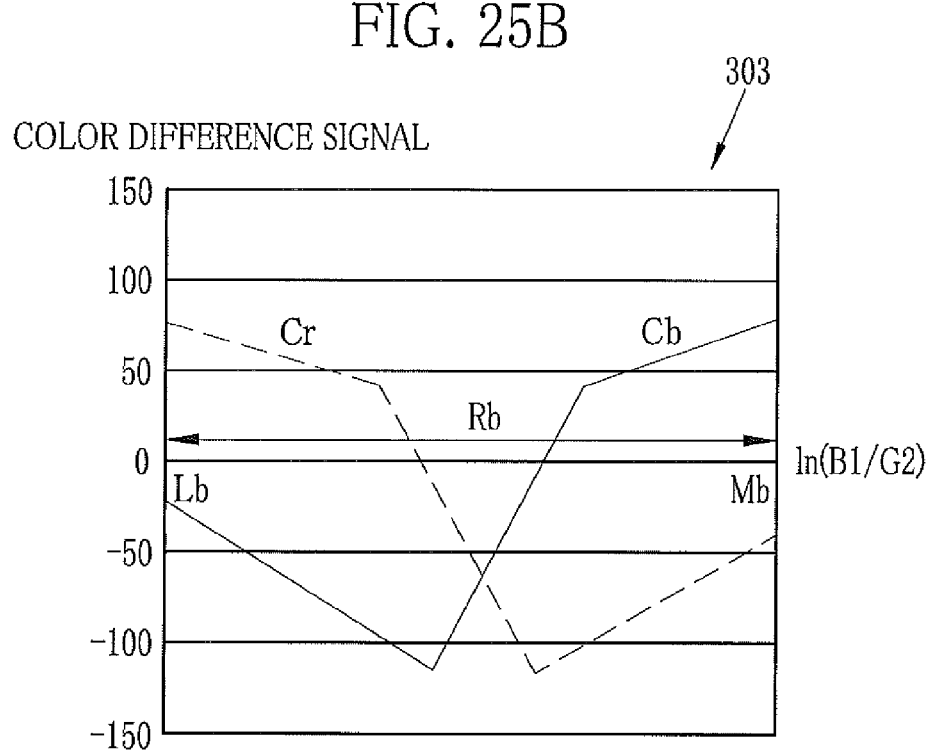
FIG. 25B is a color table illustrating a relation between the signal ratio B1/G2 and the color difference signals in a case where the signal ratio R2/G2 is less than a predetermined value.

The oxygen saturation image may be produced based on the signal ratios B1/G2 and R2/G2, without calculating the oxygen saturation level (the G2 is assigned to the luminance signal Y in a manner similar to the above embodiments). In this case, color tables 302 and 303, in each of which the signal ratios B1/G2 and B1/G2 are associated with the color difference signals Cr and Cb as shown in FIGS. 25A and 25B, are used. The color table 302 is used in a case where the signal value of the signal ratio R2/G2 is greater than or equal to a predetermined value. The color table 303 is used in a case where the signal value of the signal ratio B1/G2 is less than the predetermined value.

In consideration of light scattering properties inside living tissue and light absorption properties of oxyhemoglobin and deoxyhemoglobin, a range in which the signal value of the signal ratio B1/G2 varies in a case where the signal ratio R2/G2 is greater than or equal to the predetermined value (in a case where the blood volume is large) is greater than a range in which the signal value of the signal ratio B1/G2 varies in a case where the signal ratio B1/G2 is less than the predetermined value (in a case where the blood volume is small). Accordingly, a Range Ra (minimum value La–maximum value Ma) of the signal ratio B1/G2 in the color table 302 is greater than a range Rb (minimum value Lb–maximum value Mb) of the signal ratio B1/G2 in the color table 303. Note that changes in color of a blood vessel caused by the use of the color table 302 or 303 are similar to those caused by the use of the color table 300.

In the above embodiments, the oxygen saturation levels are visualized. Instead or in addition, an oxyhemoglobin index or a deoxyhemoglobin index may be visualized. The oxyhemoglobin index is obtained by "blood volume (sum of oxyhemoglobin and deoxyhemoglobin)×oxygen saturation level (%)". The deoxyhemoglobin index is obtained by "blood volume×(100−oxygen saturation level) (%)".

Various changes and modifications are possible in the present invention and may be understood to be within the present invention.

What is claimed is:

1. An endoscope system comprising:
a light source that sequentially applies white light and blue narrowband light in which extinction coefficient varies significantly in accordance with a change in an oxygen saturation level of hemoglobin in blood, to a subject;
a color image sensor that receives an imaging reflection light from the subject illuminated by the blue narrowband light in a first frame to obtain a first image signal, and receives an imaging reflection light from the subject illuminated by the white light in a second frame to obtain a second image signal, and a third image signal, the first image signal corresponding to first reflection light including a first wavelength range in a blue region, an extinction coefficient varying in accordance with an oxygen saturation level of hemoglobin in blood in the first wavelength range, the second image signal corresponding to second reflection light including a second wavelength range in a red region, the third image signal being used for standardizing the first and the second image signals, the third image signal corresponding to third reflection light including a third wavelength range in a green region, the third wavelength range differing from the first and the second wavelength ranges;
a processing circuitry configured for:
obtaining a first standardization signal ratio and a second standardization signal ratio, the first standardization signal ratio being obtained by standardizing the first image signal with the third image signal, the second standardization signal ratio being obtained by standardizing the second image signal with the third image signal;
calculating the oxygen saturation level from a combination of the first and second standardization signal ratios with referring to a correlation stored in a memory, the correlation being a predefined relation between the oxygen saturation and the combination of the first and second standardization signal ratios; and
producing an oxygen saturation image in which the oxygen saturation level is visualized in pseudo color, with referring to a color table stored in a memory, and
a display that displays the oxygen saturation image.

2. The endoscope system of claim 1, further comprising an oxygen saturation calculator that obtains the oxygen saturation level not dependent on the blood volume, based on the first image signal, second image signal and the third image signal, and an oxygen saturation image generator for producing the oxygen saturation image based on the oxygen saturation level obtained by the oxygen saturation calculator.

3. The endoscope system of claim 1, wherein the color image sensor images the subject, illuminated with blue narrowband light, with a color image sensor to obtain the first image signal, and the color image sensor images the subject, illuminated with white light, with the color image sensor to obtain the second image signal and the third image signal.

4. The endoscope system of claim 3, wherein the white light is pseudo white light generated by applying excitation light of a predetermined wavelength to a wavelength converter.

5. The endoscope system of claim 1, wherein the light source sequentially applies first illumination light, second illumination light, and third illumination light to the subject, and the first illumination light has the first wavelength range, and the second illumination light has the second wavelength range, and the third illumination light has the third wavelength range,
and the color image sensor receives and images reflection light of the sequentially applied first to third illumination light, with a monochrome image sensor, to sequentially obtain the first image signal, second image signal and the third image signal.

6. The endoscope system of claim 1, wherein the light source simultaneously applies first illumination light and fourth illumination light to the subject, and the first illumination light has the first wavelength range, and the fourth illumination light has the second and the third wavelength ranges, and
the color image sensor receives and images reflection light of the simultaneously applied first and the fourth illumination light with a color image sensor, to obtain the first image signal, second image signal and the third image signal.

7. The endoscope system of claim 1, wherein the first wavelength range or the second wavelength range is within a range from 460 to 700 nm.

8. The endoscope system of claim 1, wherein the first wavelength range is from 460 to 480 nm, and the second wavelength range is from 590 to 700 nm, and the third wavelength range is from 540 to 580 nm.

9. The endoscope system according to claim 1, wherein the light source sequentially applies the blue narrowband light, in which extinction coefficient of oxyhemoglobin and extinction coefficient of deoxyhemoglobin are different.

10. An endoscope system comprising:
a light source that sequentially applies white light and blue narrowband light in which extinction coefficient varies significantly in accordance with a change in an oxygen saturation level of hemoglobin in blood, to a subject;
a color sensor that receives an imaging reflection light from the subject illuminated by the blue narrowband light in a first frame to obtain a first image signal, and receives an imaging reflection light from the subject illuminated by the white light in a second frame to obtain a second image signal, and a third image signal, the first image signal corresponding to first reflection light including a first wavelength range in a blue region, an extinction coefficient varying in accordance with an oxygen saturation level of hemoglobin in blood in the first wavelength range, the second image signal corresponding to second reflection light including a second wavelength range in a red region, the third image signal being used for standardizing the first and the second image signals, the third image signal corresponding to third reflection light including a third wavelength range in a green region, the third wavelength range differing from the first and the second wavelength ranges;

a processing circuitry configured for:
obtaining a first standardization signal ratio and a second standardization signal ratio, the first standardization signal ratio being obtained by standardizing the first image signal with the third image signal, the second standardization signal ratio being obtained by standardizing the second image signal with the third image signal;
producing an oxygen saturation image with the use of a first correlation between the first standardization signal ratio and first color information and for producing a blood volume image with the use of a second correlation between the second standardization signal ratio and second color information, the oxygen saturation level being visualized in pseudo color with referring to a color table stored in a memory, the blood volume being visualized in the blood volume image; and
calculating the oxygen saturation level from a combination of the first and second standardization signal ratios with referring to a correlation stored in a memory;
the correlation being a predefined relation between the oxygen saturation and the combination of the first and second standardization signal ratios;
a display device that displays the oxygen saturation image and the blood volume image.

11. An endoscope system comprising:
a light source that sequentially applies white light and blue narrowband light in which extinction coefficient varies significantly in accordance with a change in an oxygen saturation level of hemoglobin in blood, to a subject;
a color sensor that receives an imaging reflection light from the subject illuminated by the blue narrowband light in a first frame to obtain a first image signal, and receives an imaging reflection light from the subject illuminated by the white light in a second frame to obtain a second image signal and a third image signal, the first image signal corresponding to first reflection light including a first wavelength range in a blue region, an extinction coefficient varying in accordance with an oxygen saturation level of hemoglobin in blood in the first wavelength range, the third image signal corresponding to third reflection light including a third wavelength range in a green region, the third image signal being used for standardizing the first image signal, the third wavelength range differing from the first wavelength range;
a processing circuitry configured for:
obtaining a first standardization signal ratio and a second standardization signal ratio, the first standardization signal ratio being obtained by standardizing the first image signal with the third image signal, the second standardization signal ratio being obtained by standardizing the second image signal with the third image signal;
producing an oxygen saturation image with the use of a first correlation between the first standardization signal ratio and first color information, the oxygen saturation level being visualized in pseudo color with referring to a color table stored in a memory; and
calculating the oxygen saturation level from a combination of the first and second standardization signal ratios with referring to a correlation stored in said memory;
the correlation being a predefined relation between the oxygen saturation and the combination of the first and second standardization signal ratios; and
a display device that displays the oxygen saturation image.

12. A processor device used with an endoscope device for receiving and imaging reflection light from a subject illuminated with a light source, the light source sequentially applying white light and blue narrowband light in which extinction coefficient varies significantly in accordance with a change in an oxygen saturation level of hemoglobin in blood, to said subject, to obtain a first image signal, and receives an imaging reflection light from the subject illuminated by the white light in a second frame to obtain a second image signal, and a third image signal, the first image signal corresponding to first reflection light including a first wavelength range in a blue region, an extinction coefficient varying in accordance with an oxygen saturation level of hemoglobin in blood in the first wavelength range, the second image signal corresponding to second reflection light including a second wavelength range in a red region, the third image signal being used for standardizing the first and the second image signals, the third image signal corresponding to third reflection light including a third wavelength range in a green region, the third wavelength range differing from the first and the second wavelength ranges;
the processor device further configured for:
obtaining a first standardization signal ratio and a second standardization signal ratio, the first standardization signal ratio being obtained by standardizing the first image signal with the third image signal, the second standardization signal ratio being obtained by standardizing the second image signal with the third image signal;
calculating the oxygen saturation level from a combination of the first and second standardization signal ratios with referring to a correlation stored in a memory;
producing an oxygen saturation image in which the oxygen saturation level is visualized in pseudo color with referring to a color table stored in said memory;
wherein a correlation between a first color information and a combination of the first and second standardization signal ratios to produce the oxygen saturation image;
wherein the correlation is a predefined relation between the oxygen saturation and the combination of the first and second standardization signal ratios, and
receiving the first image signal, second image signal and third image signal from the endoscope device.

13. A method for operating an endoscope system comprising the steps of:
sequentially applying white light and blue narrowband light in which extinction coefficient varies significantly in accordance with a change in an oxygen saturation level of hemoglobin in blood, to a subject;
applying illumination light from a light source;
obtaining first to third image signals, the first to the third image signals being obtained by receiving and imaging reflection light from a subject with an imaging device, the first image signal corresponding to first reflection light including a first wavelength range in a blue region, an extinction coefficient varying significantly in accordance with an oxygen saturation level of hemoglobin in blood in the first wavelength range, the second image signal corresponding to second reflection light including a second wavelength range in a red region, the third image signal being used for standardizing the first and the second image signals, the third image signal corresponding to third reflection light including a third wavelength range in a green region, the third wavelength range differing from the first and the second wavelength ranges;

obtaining a first standardization signal ratio and a second standardization signal ratio, the first standardization signal ratio being obtained by standardizing the first image signal with the third image signal, the second standardization signal ratio being obtained by standardizing the second image signal with the third image signal;

producing an oxygen saturation image based on the first to the third image signals with the use of an oxygen saturation image generator, the oxygen saturation level being visualized in the oxygen saturation image; and displaying the oxygen saturation image on a display device, wherein the image generator uses a correlation between a first color information and a combination of the first and second standardization signal ratios to produce the oxygen saturation image;

wherein the correlation is a predefined relation between the oxygen saturation and the combination of the first and second standardization signal ratios.

* * * * *